United States Patent [19]

Yu et al.

[11] Patent Number: 5,733,748
[45] Date of Patent: Mar. 31, 1998

[54] COLON SPECIFIC GENES AND PROTEINS

[75] Inventors: Guo-Liang Yu, Darnestown; Craig Rosen, Laytonsville, both of Md.

[73] Assignee: Human Genome Sciences, Inc., Rockville, Md.

[21] Appl. No.: 469,667

[22] Filed: Jun. 6, 1995

[51] Int. Cl.$^6$ .................................................. C07H 21/04
[52] U.S. Cl. ...................... 435/70.1; 536/22.1; 536/23.5; 435/325; 435/252.3; 435/320.1
[58] Field of Search ................................ 536/22.1, 23.5; 435/70.1, 325, 252.3, 320.1

[56] References Cited

PUBLICATIONS

Science, vol. 263, issued 18 Mar. 1994, Papadopoulos et al., "Mutation of a nutL Homolog in Hereditary Colon Cancer", pp. 1625–1629, see entire document.

The Journal of Biological Chemistry, vol. 269, No. 4, issued 28 Jan. 1994, Gum. Jr. et al, "Molecular Cloning of Human Intestinal Mucin (MUC2) cDNA", pp. 2440–2446, see entire document.

The Journal of Biological Chemistry, vol. 267, No. 30, issued 25 Oct. 1992, Gum, Jr. et al. "The Human MUC2 Intestinal Mucin Has Cysteine–rich Subdomains located Both Upstream and Downstream of its Central Repetitive Region", pp. 21375–21383, see entire document.

Advances in Brief, TJU, 1025, Walnut Street, Suite 1112, Philadelphia, P.A., Moreno, et al., "Detection of Hematogenous Micrometastasis in Patients with Prostate Cancer", pp. 6110–6112.

The Journal of Biological Chemistry, vol. 267, No. 8, issued 15 Mar. 1992, Xu et al., "cDNA for the Carboxyl–terminal Region of a Rat Intestinal Mucin–like Peptide", pp. 5401–5407, see entire document.

Lowe et al. Structure and Methylation pattern of the gene encoding human carbonic anhydrant I Gene, 1990, 93, 277–283.

database : Swiss–prot32.
database : accession No. JQ0786; ACQ02817.

Primary Examiner—Kenneth R. Horlick
Assistant Examiner—Joyce Tung
Attorney, Agent, or Firm—Elliot M. Olstein; J.G. Mullins

[57] ABSTRACT

Human colon specific gene polypeptides and DNA (RNA) encoding such polypeptides and a procedure for producing such polypeptides by recombinant techniques is disclosed. Also disclosed are methods for utilizing such polynucleotides or polypeptides as a diagnostic marker for colon cancer and as an agent to determine if colon cancer has metastasized. Also disclosed are antibodies specific to the colon specific gene polypeptides which may be used to target cancer cells and be used as part of a colon cancer vaccine. Methods of screening for agonists and antagonists for the polypeptide and therapeutic uses of the antagonists are disclosed.

20 Claims, 17 Drawing Sheets

FIG. 1

GCCAGGCAGCTGGCTGCCSACCAGGCCGTGTATGTGAAGGTCAAGGCTGAAGCCCGGGAA
 A  R  Q  L  A  A  X  Q  A  V  Y  V  K  V  K  A  E  A  R  E

CTGCTGGGCCACCCGTGGTCTCTGTGTCCTGTGTGGGTGCCAACTCACCACCTTTGAT
 L  L  G  H  P  W  S  L  C  P  V  C  G  Q  L  T  T  F  D

GGGGCCCGTGGTGCCACCACTCTCCTGGTGTCTATGAAGCTCTTCCCGCTGCCAGGA
 G  A  R  G  A  T  T  L  L  V  S  M  K  L  S  S  R  C  P  G

CTACAGAATACCATCCCCTGTACCGTGTAGTTGCCGAAGTCCAGATCTGCCATGGCAAA
 L  Q  N  T  I  P  W  Y  R  V  V  A  E  V  Q  I  C  H  G  K

ACGGAGGCTGTGGGCCAGTCCACATCTTCTTCCAGGATGGTATGGTGACTCCA
 T  E  A  V  G  Q  V  H  I  F  F  Q  D  G  M  V  T  L  T  P

AACAAGGGTGTGTGGGTGAATGGTCTCCGAGTGGATCTCCCAGCTGAGAAGTTAGCATCT
 N  K  G  V  W  V  N  G  L  R  V  D  L  P  A  E  K  L  A  S

GTGTCCCGTGAGTCCGTACACCTGGATGGCTCCCTGCTAGTCCGCCAGAAGGCAGGGTCCAG
 V  S  V  S  R  T  P  D  G  S  L  L  V  R  Q  K  A  G  V  Q
GTGTGGCTTGAGCAATGGAAGGTGCTGTGATTGTGAGCAATGACCATGCTGGAAAA
 V  W  L  G  A  N  G  K  V  A  V  I  V  S  N  D  H  A  G  K

CTGTGTGGGGCCTKTGAAAATTTGACGGGAACTTTCTYCCMCATGTTAATGG
 L  C  G  G  L  W  K
AGGAGAAGCCAGCGATTGGGGAAWTGGAGAGCCAGGACTTTCTYCCMCATGTTAATGG

GCTTGWTCCAGTTCATCCCACCAGGAACGAAGGATTTT

FIG. 2A

```
CAGGACTGCGTGTGCACGGACAAGGTGGACAACACCCTGCTCAACGTCATCGCCTGC
 Q  D  C  V  C  T  D  K  V  D  N  T  L  L  N  V  I  A  C

ACCCACGTGCCCTGCAACACTTCCTGCAGCCCCGGGTTCGAACTCATGGAGGCCCCGGG
 T  H  V  P  C  N  T  S  C  S  P  G  F  E  L  M  E  A  P  G

GAGTGCTGTAAGAAGTGTGAACAGACGCACTGTATCATCAAGCGCCCAGACAACCAGCAC
 E  C  C  K  K  C  E  Q  T  H  C  I  I  K  R  P  D  N  Q  H

GTCATCCTGAAGCCCGGGGACTTCAAGAGCGACCCGAAGAACAACTGCACATTCTTCAGC
 V  I  L  K  P  G  D  F  K  S  D  P  K  N  N  C  T  F  F  S

TGCGTGAAGATCCACAACCAGCTCATCTCGTCCGTTTCCAACATCACCTGCCCCAACTTT
 C  V  K  I  H  N  Q  L  I  S  S  V  S  N  I  T  C  P  N  F

GATGCCAGCATTTGCAATGAGACTCGGGTGCCAATCATGCCCAATGGATGCTGCAAGACC
 D  A  S  I  C  I  P  G  S  I  T  F  M  P  N  G  C  C  K  T

TGCACCCCTCGCAATGAGACCAGGGTGCCCTGCTCCACCGTCCCGGTGACCACGGAGGTT
 C  T  P  R  N  E  T  R  V  P  C  S  T  V  P  V  T  T  E  V

TCGTACGCCGGCTGCACCAAGACCAAGGTCCTCATGAATCATTGCTCCGGTTGCGGGACA
 S  Y  A  G  C  T  K  T  K  V  L  M  N  H  C  S  G  C  G  T
```

FIG. 2B

```
TTTGTCATGTACTCGGCCAAGGCCCAGGCCCTGGACCACAGCTGCTGCTGCAAAGAG
 F  V  M  Y  S  A  K  A  Q  A  L  D  H  S  C  C  C  K  E

GAGAAAACCAGCCAGCGGTGAGGTGGTCCTGAGCTGCCCCAATGGCGGCTCGACACAC
 E  K  T  S  Q  R  E  V  V  L  S  C  P  N  G  G  S  L  T  H

ACCTACACCCACATCGAGAGCTGCCAGTGCCAGGACACCGTCTGGGGCTCCCCACCGGC
 T  Y  T  H  I  E  S  C  Q  C  Q  D  T  V  C  G  L  P  T  G

ACCTCCCGCGGGCGGCGTTCCCCTAGGCATCTGGGGCATCCCCCGACCCTCTGAGCCTCCTAAGCT
 T  S  R  R  A  R  R  S  P  R  H  L  G  S  G

CAGCCCCTTCACTGCCCTCGACAGCTTTACCTCCCCCGACCCTCTGAGCCTCCTAAGCT

CGGCTTCCTCTCTTCAGATATTTATTGTCTGAGTTTTTGTTCAGTCCTTGCTTTCCAATA

ATAAACTCAGGGGACATGCAAAAAAAAAAAAA
```

FIG. 3A

```
ATTGGGTGCTACCTGGCTCTCCTGTCTCTGCAGCTCTACAGGTGAGCCCAGCAGAGGGAG
TAGGGCTCGCCATGTTTCTGGTGAGCCAATTGGCTGATCTTGGCGTGTCTGAACAGCTAT
TGGGTCCACCCAGTCCCTTTCAGCTGCTTAATGCCCTGCTCTCTCCCTGCCACC
TTATAGAGAGCCCAAAGAGCTCCGTAAGAGGAGAACTCTATCTGTGTTTATAATCTT
GCACGGAGCCACCAGAAGTCTCCCTGTGAATGAACTACATTTATCCCCTTTCCT
GCCCCAACCACAAACTCTTCCTTCAAAGAGGCCTGCTGGTTCCCTCCACCAACTGC
ACCATGAGATCGGTCCAAGAGTCCATTCCCAGGTGGGAGCCAACTGTCAGGGAGTCTT
TCCCACCAAACATCTTTCAGTTGCTGTGGGAGGTGACCATAGGGCTCTGCTTTAAGATAT
GGCTGCTTCAAAGGCCAGAGTCACAGGAAGGACTCTTCCAGGAGATTAGTGGTGATGG
AGAGGAGAGTTAAAATGACCTCATGTCCTTCTGTCCACGGTTTTGTGAGTTTCACTC
TTCTAATGCAAGGTCTCACACTGTGAACCACTTAGGATGTGATCACTTTCAGGTGGCCA
GGAATGTTGAATGTCTTTGCTCAGTTCATCTAAAAAGATATCTATTTGAAAGTTCTCA
```

FIG. 3B

GAGTTGTACATATGTTCACAGTACAGGATCTGTACATAAAGTTTCTTCCTAAACCAT

TCACCAAGAGCCAATATCTAGGCATTTCCTCGGTAGCACAAATTTCTNATTGCTTAGAA

AATTGTCCCTCCCTGTTCTTTCTGTCTGNAGACTTAAGTGAGTTAGTCTTTAAGGAAAGC

AACGCTCCTCTGAAATGCTTGTCTTTTTTCTGTTGCCGAAATAGCTGTCCTTTTTCGGG

AGTTAGATGTATAGAGTGTTTGTATGTAAACATTTCTTGTAGCCATCACCATGAACANAG

ATATATTTCTATTTANTTANTATATGTGCACTTCAAGAAGTCACTGTCAGAGAATAAA

GAATTGTCTTAAATGTCATGATTGGAGATGTCCTTTGCATTGCTTGGAAGGGGTGTACCT

AGAGCCAAGGAAATTGGCTCTGGTTTGGAAAAATTTGCTGTTATTATAGTAAACATACA

AAGGATGTC

FIG. 4

```
ATGAGTCCTGTGAAAAACAATGTGGGCAGAGGCCTAAACATCGCCCTGGTGAATGGAACC
 M  S  P  V  K  N  N  V  G  R  G  L  N  I  A  L  V  N  G  T

ACGGGAGCTGTGCTGGGACAGAAGGCATTTGACATGTACTCTGGAGATGTTATGCACCTA
 T  G  A  V  L  G  Q  K  A  F  D  M  Y  S  G  D  V  M  H  L

GTGAAATTCCTAAAGAAATTCCGGGGGGTGCACTGGTGGTGGCCTCCTACGACGAT
 V  K  F  L  K  E  I  P  G  G  A  L  V  L  V  A  S  Y  D  D

CCAGGGACCAAAATGAACGATGAAAGCAGGAAACTCTTCTCTGACTTGGGAGTTCCTAC
 P  G  T  K  M  N  D  E  S  R  K  L  F  S  D  L  G  S  S  Y

GCAAAACAACTGGGCTTCCGGGACAGTTGGGTCTTCATAGGAGCCAAAGACCTCAGGGGT
 A  K  Q  L  G  F  R  D  S  W  V  F  I  G  A  K  D  L  R  G

AAAAGCCCCTTTGAGCAGTTCTTAAAGAACAGCCCAGACACAAACAAATACGAGGGATGG
 K  S  P  F  E  Q  F  L  K  N  S  P  D  T  N  K  Y  E  G  W

CCAGAGCTGCTGGAGATGGAGGGCTGCATGCCCCCGAAGCCATTTTAGGTGGCTGTGGC
 P  E  L  L  E  M  E  G  C  M  P  P  K  P  F

TCTTCCTCAGCCAGGGCCTGAAGAAGTCCTGCCTGCATTAGGAGTCANAGCCCGGGCAG

GCTGNAGGAGGAGGAGCAGGGGTGCTGCGTGGAAGCTGCTGCAGCCCTTGCACGCTGTG

TCGGCCT
```

FIG. 5A

```
TGTCTACTCAAGGTATTCACAACTTATGACACGAATGGTAGATACAGTGTAAAAGTGCG
 V  Y  S  R  Y  F  T  T  Y  D  T  N  G  R  Y  S  V  K  V  R

GGCTCTCGGAGGAGTTAACGCAGCCAGACGGAGAGTGATACCCCAGCAGTGGAGCACT
 A  L  G  G  V  N  A  A  R  R  R  V  I  P  Q  Q  S  G  A  L

GTACATACCTGCTGGATTGAGAATGATGAAATACAAGGACCTGAAT
 Y  I  P  G  W  I  E  N  D  E  I  Q  W  N  P  P  R  P  E  I

TAATAAGGATGATGTTCAACACAAGCAAGTGTGTTTCAGCAGAACATCTCGGAGGCTC
 N  K  D  D  V  Q  H  K  Q  V  C  F  S  R  T  S  G  G  S

ATTTGTGGCTTCTGATGTCCCAAATGCTCCCATACCTCCTGATCTCTTCCCACTGGCCAAT
 F  V  A  S  D  V  P  N  A  P  I  P  P  D  L  F  P  P  G  Q  I

CACCGACCTGAAGGCGGAAATTCACGGGGCAGTCTCATTAATCTGACTTGGACAGCTCC
 T  D  L  K  A  E  I  H  G  G  S  L  I  N  L  T  W  T  A  P

TGGGGATGATTATGACCATGGAACAGCTCACAAGTATATCATTCGAATAAGTACAAGTAT
 G  D  D  Y  D  H  G  T  A  H  K  Y  I  I  R  I  S  S  I

TCTTGATCTCAGAGACAAGTTCAATGAATCTCTTCAAGTGAATACTACTGCTCTCATCCC
 L  D  L  R  D  K  F  N  E  S  L  Q  V  N  T  T  A  L  I  P
```

FIG. 5B

```
AAAGGAAGCCAACTCTGAGGAAGTCTTTTTGTTTAAACCAGAAAACATTACTTTTGAAAA
 K  E  A  N  S  E  E  V  F  L  F  K  P  E  N  I  T  F  E  N

TGGCACAGATCTTTCATTGCTATTCAGGCTGTTGATAAGTCGATCTGAAATCAGAAAT
 G  T  D  L  F  I  A  I  Q  A  V  D  K  V  D  L  K  S  E  I

ATCCAACATTGCACGAGTATCTTTGTTATTCCTCCACAGACTCCGCCAGAGACACCTAG
 S  N  I  A  R  V  S  L  F  I  P  P  Q  T  P  P  E  T  P  S

TCCTGATGAAACGTCTCGCTCCTGTGCCTAATATATCATCAACAGCACCATTCCTGGCA
 P  D  E  T  S  A  P  C

TTCACATTTAAAAATTATGTGGAAGTGGTAGGAGAACTGCAGTTGTCAATAGNCTAGG

GGTGAATTTTGTGCGGTGAATAAATSATTCANCCTTTTTTTGRTTTATAAAAAAA

CGGNTNCCCATTGGGNNTNTNGNGGGGGGGNNTTTTAA
```

FIG. 6

```
AGTCGCTCTCCTAGCCCTTCTGTGCCTCACCCTGCAATGCCATTCAGGCCAGTC
 V  A  L  L  A  L  L  C  A  S  P  S  G  N  A  I  Q  A  R  S

TTCCTCCTATAGTGGAGAGTATGGAGGTGTGGAAGCGATTCTCTCATTCTGCAA
 S  S  Y  S  G  E  Y  G  G  G  G  G  K  R  F  S  H  S  G  N

CCAGTTGGACGGCCCCATCACCGCCCTCCGGGTCCGAGTCAACACATACTATCGTAGG
 Q  L  D  G  P  I  T  A  L  R  V  R  V  N  T  Y  Y  I  V  G

TCTTCAGGTGCGCTATGGCAAGGTGTGGAGCGACTATGTGGTGTCGCAACGGAGACCT
 L  Q  V  R  Y  G  K  V  W  S  D  Y  V  V  G  G  R  N  G  D  L

GGAGGAGATCTTTCTGCACCCTGGGAATCAGTGATCAGTTTCTGGAAGTACAAGTG
 E  E  I  F  L  H  P  G  E  S  V  I  Q  V  S  G  K  Y  K  W

GTACCTGAAGAAGCTGGTATTTGTGACAGACAAGGGCCGCTATCTGTCTTTTGGAAAGA
 Y  L  K  K  L  V  F  V  T  D  K  G  R  Y  L  S  F  G  K  D

CAGTGGCACAAGTTTCAATGCCGTTCATGATGCCGTGCACTGGGATGTTTACCCCACTAG
 S  G  T  S  F  N  A  V  P  L  H  P  N  T  V  L  R  F  I  S

TGGCCGGTCTGGTTCTCTCATCGATGCCATTGGCCTGCACTGGGATGTTTACCCCACTAG
 G  R  S  G  S  L  I  D  A  I  G  L  H  W  D  V  Y  P  T  S
CTGCAGAGATGCTGAGCCTCCTCTTGGCAGGGCACTGTGATGAGGAGTAAGAACT
 C  S  R

CCTTATCACTAACCCCCATC
```

FIG. 7

TAAACTGCTGTGTTTGTTCCTGTGTCTGTTTGGTTGGTATTTCAGTAAGTTTTTGT
ATTCTCAAATTTATCTAAATGGATAAACTATTAACATAGAACATAAACCCAATTCTCC
ATTTCATTTTCTCTTAGGCATGAATCATACAAAACTCAATATAGAGCAATGTTTGTAAT
GAATTGTTCTATTAACAAAGAGGAGGTCTAAGATATATAAGCCTCAGAGAACAGGAAGAA
AAGGCGGGTCCATAAGAAGATGAGGTCTAACCGGAAGATGCTGAGAAGGCAGAGAC
AGATGTGGAAGAAATCTATCACCCAGTCATGCCACTGAATGTCCACTGAAGTGGCAGT
TTACGACAAGGATGAAGTCTTTCATTTTCAATGTTTAGCAAGCCATTCCTAAACAGC
CCAACTGGCATTAATTACCCAATACTGTATATAAGGCAAATATGGACAGTTACTTCCT
CTTGCCTGTGTTCATATCCTTCAGTGACATTGAGGAAGCAGTGTTCTCTTTTTAAGGGGA
ATAGTTGTCAACCTTCATTCATCTCTTACATCTTTCACCCTCTCCTTTTTTTTTCTTTG
ATTTCCCCTTATTGATGGACTGATATTCATTCATCGTTTTTGATGAACATTTGGAAACT
GTCGGGCTTTTATTAAGCTCTGTAGAATTAAAATGTTCTGGAATTAT

FIG. 8

CAGGAGGAGAGCCTTCCCCAAGCAACAATCCAGAGCAGCTGTGCAAACAACGGTGCAT

AAATAAGCCTCCTGACCATGAATGCGAGTCCCTGAGTCCCTGCGTACCGGAGCCCACGGT

GGTCATGGCTGCCAGAGCGCTCATGCTGGGCCTGTCTGCAAACCAGTGTGCCAGCAAGGACAG
 M  A  A  R  A  L  C  M  L  G  L  V  L  A  L  L  S  S  S

CTCTGCTGAGGAGTACGTGGGCTACCCCCATGTCACCCCAAGGAGTGCAACAACCGGGCTGCTT
 S  A  E  E  Y  V  G  L  S  A  N  Q  C  A  V  P  A  K  D  R

GGTGGACTGCGGCTACCCCCATGTCACCCCAAGGAGTGCAACAACCGGGCTGCTT
 V  D  C  G  Y  P  H  V  T  P  K  E  C  N  N  R  G  C  C  F

TGACTCCAGGATCCCTGGAGTGCCTTGGTGTTCAAGCCCCTGACAGGGAAGCAGGAATG
 D  S  R  I  P  G  V  P  W  C  F  K  P  L  T  G  K  Q  E  C

CACCTTCTGAGGCACCTCCAGCTGCCCCCGGCCGATGCGAGGCTCGGAGCACCCT
 T  F  *

TGCCCCGGCTGTGATTGCTGCCAGGCACTGTTCATCTCAGCTTTTCTGTCCCTTGCTCCC

GGAAGCGCTTCTGCTGAAAGTTCATATCTGGAGCCTGATGTTTAACGTAGTCCCATGCTC

CACCCGAAAAAAAAAAAAAAAAAAAAAAA

FIG. 9A

```
AAGCTCTTCTCACAGGACCAGCCACTAGCGCAGCTCGAGGATGGCCTATGTCCCGCAC
                                  M  A  Y  V  P  A  P

CGGGCTACCAGCCCACTTACAACCCGACCCTGCCTTACTACCAGCCCATCCCGGCGGGC
 G  Y  Q  P  T  Y  N  P  T  L  P  Y  Y  Q  P  I  P  G  G  L

TCAACGTGGGAATGTCTGTTACATCCAAGGAGTGGCCAGCGAGCACATGAAGCGGTTCT
 N  V  G  M  S  V  Y  I  Q  G  V  A  S  E  H  M  K  R  F  F

TCGTGAACTTTGTGGTTGGTCAGGATCCGGGCTCAGACGTTGCCTTCCACTTCAATCCGC
 V  N  F  V  V  G  Q  D  P  G  S  D  V  A  F  H  F  N  P  R

GGTTTGACGGCTGGGACAAGGTGTCTTCAACACGTTGCAGGGCGGGAAGTGGGGCAGCG
 F  D  G  W  D  K  V  V  F  N  T  L  Q  G  G  K  W  G  S  E

AGGAGAGGAAGAGGAGCATGCCCTTCAAAAAGGGTCCCGCCTTTGAGCTGGTCTTCATAG
 E  R  K  R  S  M  P  F  K  K  G  A  A  F  E  L  V  F  I  V

TCCTGGCTGAGCACTACAAGGTGGTGTAAATGGAAATCCCTTCTATGAGTACGGGCACC
 L  A  E  H  Y  K  V  V  N  G  N  P  F  Y  E  Y  G  H  R

GGCTTCCCCTACAGATGGTCACCCACCTGCAAGTGGATGGGGATCTGCAACTTCAATCAA
 L  P  L  Q  M  V  T  H  L  Q  V  D  G  D  L  Q  L  Q  S  I

TCAACTTCATCGGAGGCCAGCCCCTCCGGCCCCAGGGACCCCCGATGATGCCACCTTACC
 N  F  I  G  G  Q  P  L  R  P  Q  G  P  P  M  M  P  P  Y  P
```

FIG. 9B

```
CTGGTCCCGGACATTGCCATCAACAGCTGAACAGCCTGCCCACCATGGAAGGACCCCAA
 G  P  G  H  C  H  Q  Q  L  N  S  L  P  T  M  E  G  P  P  T

CCTTCAACCCCCTGTGCCATATTTCGGAGGGCTGCAAGGGCTCACAGCTGAAGAA
 F  N  P  P  V  P  Y  F  G  R  L  Q  G  G  L  T  A  R  R  T

CCATCATCATCAAGGGCTATGTGCCTCCCACAGGCAAGAGCTTTGCTATCAACTTCAAGG
 I  I  I  K  G  Y  V  P  P  T  G  K  S  F  A  I  N  F  K  V

TGGGCTCCTCAGGGGACATAGCTCTGCACATTAATCCCGCATGGGCAACGGTACCGTGG
 G  S  S  G  D  I  A  L  H  I  N  P  R  M  G  N  G  T  V  V

TCCGGAACAGCCTTCTGAATGGCTCGTGGGGATCCGAGGAGAAGAAGATCACCACAACC
 R  N  S  L  L  N  G  S  W  G  S  E  E  K  K  I  T  H  N  P

CATTGGTCCCGGACAGTTCTTTGATCTGTCCATTCGCTGTGGCTTGGATCGCTTCAAGG
 F  G  P  Q  F  F  D  L  S  I  R  C  G  L  D  R  F  K  V

TTTACGCCAATGGCCAGCACCTCTTTGACTTTGCCCATCGCCTCTCGGCCTTCCAGAGGG
 Y  A  N  G  Q  H  L  F  D  F  A  H  R  L  S  A  F  Q  R  V

TGGACACATTGGAAATCCAGGGTGATGTCACCTTGTCCTATGTCCAGATCTAATCTATTC
 D  T  L  E  I  Q  G  D  V  T  L  S  Y  V  Q  I
CTGGGGCCATAACTCATGGAAACAGAATTATCCCCTAGGACTCCTTTCTAAGCCCCTA

ATAAATGTCTGAGGGTGTCTCAAAAAAAAAAAAAAAAA
```

FIG. 10

```
GTTGATATTAAAACCAGTGAAACCAAGACACCTCTCTGAACCTATTAGTGTCTCC
 V  D  I  K  T  S  E  T  K  H  D  T  S  L  K  P  I  S  V  S

TACAACCCAGCCACAGCCAAAGAATTATCAATGTGGGGCATTCCTTCCATGTAAATTT
 Y  N  P  A  T  A  K  E  I  I  N  V  G  H  S  F  H  V  N  F

GAGGACAACGATAACCGATCAGTGCTGAAAGGTGGTCCTTTCTTCTGACAGCTACAGGCTC
 E  D  N  D  N  R  S  V  L  K  G  G  P  F  F  L  T  A  T  G  L

TTTCAGTTCCATTTTCACTGGGGCAGTACAAATGAGCATGGTTCAGAACATACAGTGGAT
 F  Q  F  H  F  H  W  G  S  T  N  E  H  G  S  E  H  T  V  D

GGAGTCAAATATTCTGCCGAGCTTCACGTGGCTCACTGGAATTCGCAAAGTACTCCAGC
 G  V  K  Y  S  A  E  L  H  V  A  H  W  N  S  A  K  Y  S  S

CTTGCTGAAGCTGCCTCAAAGGCTGATGGTTTGGCAGTTATTGGTGTTTTGATGAAGTT
 L  A  E  A  A  S  K  A  D  G  L  A  V  I  G  V  L  M  K  V

GGTGAGGCCAACCCAAAGCTGCAGAAAGTACTTGATGCCCTCTACTCTCCTTCATCCCAAG
 G  E  A  N  P  K  L  Q  K  V  L  D  A  L  Q  A  I  K  T  K

GGCAAACGAGCCCCATTCACAAATTTTGACCCTCCTACTCTCCTTCATCCCTGGAT
 G  K  R  A  P  F  T  N  F  D  P  S  T  L  L  P  S  S  L  D

TTCTGACCTACCCTGGCTCTCTGACTCATCCTCCTCTTTATGAGAGTGTAACTTGGATC
 F  W  T  Y  P  G  S  L  T  H  P  P  L  Y  E  S  V  T  W  I

ATCTGTAAGGAGAGCATCAGTGTCAGTTCAGAGCAGTTGGCACAATTCCGGAGCCTTCTA
 I  C  K  E  S  I  S  V  S  S  E  Q  L  A  Q  F  R  S  L  L

TCAAT
 S
```

FIG. 11

```
CGGCTCCGGGGCCGGTGGCCAGTGACTAGAAGGCGAGGCGCCGCGGGACCATGGCGCG
          G  S  G  R  A  W  P  V  T  R  R  R  G  A  A  G  P  W  R  R

GCGGCGGACGAGCGGAGTCCAGAGGCCGAGAAGACGAGGAGGAGGAGCAGTTGGTTCT
 R  R  T  S  G  V  Q  R  R  E  D  E  E  E  E  E  Q  L  V  L

GGTGGAATTATCAGGAATTATTGATTCAGACTTCCTCAAAATGTGAAAATAAATGCAA
 V  E  L  S  G  I  I  D  S  D  F  L  S  K  C  E  N  K  C  K

GGTTTTGGCATTGACACTGAGAGGCCCATTCTGGCAATGGACAGCTGTGTCTTTGCTGG
 V  L  G  I  D  T  E  R  P  I  L  A  M  D  S  C  V  F  A  G

GGAGTATGAAGACACTCTAGGGACCTGTGTTATATTTGAAGAAAATGTTGAACATGCTGA
 E  Y  E  D  T  L  G  T  C  V  I  F  E  E  N  V  E  H  A  D

TACAGAAGGCAATAATAAAACAGTGCTAAAAATATAAGCCATACAATGAAGAAGCTCAG
 T  E  G  N  N  K  T  V  L  K  Y  K  C  H  T  M  K  K  L  S

CATGACAAGAACTCTCCTGACAGAGAAGGAGAAGAAACATAGTGGGGTGA
 M  T  R  T  L  L  T  E  K  K  E  G  E  E  N  I  G  G  V  E

ATGGCTGCAAATAAGGATATGTTTCTCCCTTTGACCCAACAGTTTGTTAACTTTTCTA
 M  L  Q  I  R  I  W  F  L  P  L  T  Q  Q  V  C

CCATGAAATTGAGACGAGAAGTGTAGCTTTCAGCCCCCGTAAATCTTTGATTTGG

AGGGGTGGGTTTCAATG
```

FIG. 12

GTGGCAGAAGAAAGATAGGTTGGAGAGACAATTGATTGCTCGATGATATAAAATGTTAAGTA

CCATGAATGNATGCTGTTAGGCTGGAATGCGCCAAGATAAAAGGTGGGGCATGGCATCAA

AAGGTAGGTCAACATATTAAATTCCATGTATTGAAATATCCAGAAATATATAGACA

GATCTATAGAGATAGAAACTGTCTCGCCCAGGACTAGGGGTGTCTAAGGATAAGGAGCT

TCTTTTTTGGATGGTGAAATAACCTAAAATATATTGTGCCATTGTTTGCACAACTTTGTG

GAATATATTAAAAACCGGTTAATTGTACTCACTAAAATGTCCTCCTTCTTAAATTTAAGC

TGTTTNCTGGACAAGAAAAGGGAAAGNNACCAAGGGGNAAAAATTTT

FIG. 13

```
GCCCTGGGCTTTGGGGGGTCCCAAACATGGTATGCAGAAATGTGATGGTTACAGGTCAG
TACAACCTCAGTCCCTTAGAACCCCTCCACACTTCAGCTCTGCACCCACTTCCTGTCATT
TATTTATATAGGACTGTAGTTTTTTAGTTCGAGAGCCTTTCGAAGCTTAATTTATATT
CTTTCTTGTACCTTTTTCTAAATTACCAAAGATATTACACAAAGGTAAATTAATGTT
CTCTGTTTATGCTTTATCTGATGGAGGCAAATATCCTCTATTGTTGATCAAGGGGC
AAAGAATTTAGAGGCAAATGAACAAGCGATAGGCTATTGCAACCTGAGAAAGAGAACTG
NTCCTTCCATCGTAAATTTAGNAGNCCAAGTAGTAATGGAACCAAAGTTGTTACTTT
TTCTAGTAGTTATTTTCCCTTTTNNTTTTTGTGTACCTCTTACAGNGNCCCAAACT
CCATTCTCTTAAAGGGGTTTTATGGGGCTTACTGCAGGTTAAAAATTGGGNCCAC
CATTTTTAAAGGGGGCTACCAGAAGGGAGGGGTCCCCNTTNCNAAAAAAAATTG
```

COLON SPECIFIC GENES AND PROTEINS

This invention relates to newly identified polynucleotides, polypeptides encoded by such polynucleotides, and the use of such polynucleotides and polypeptides for detecting disorders of the colon, particularly the presence of colon cancer and colon cancer metastases. The present invention further relates to inhibiting the production and function of the polypeptides of the present invention. The thirteen colon specific genes of the present invention are sometimes hereinafter referred to as "CSG1", "CSG2" etc.

The gastrointestinal tract is the most common site of both newly diagnosed cancers and fatal cancers occurring each year in the U.S.A., figures are somewhat higher for men than for women. The incidence of colon cancer in the U.S.A. is increasing, while that of gastric cancer is decreasing, cancer of the small intestine is rare. The incidence of gastrointestinal cancers varies geographically. Gastric cancer is common in Japan and uncommon in the United States, whereas colon cancer is uncommon in Japan and common in the U.S.A. An environmental etiologic factor is strongly suggested by the statistical data showing that people who move to a high-risk area assume the high risk. Some of the suggested etiologic factors for gastric cancer include aflatoxin, a carcinogen formed by *aspergillus flavus* and present in contaminated food, smoked fish, alcohol, and Vitamin A and magnesium deficiencies. A diet high in fat and low in bulk, and, possibly, degradation products of sterol metabolism may be the etiologic factors for colon cancer. Certain disorders may predispose to cancer, for example, pernicious anemia to gastric cancer, untreated non-tropical sprue and immune defects to lymphoma and carcinoma, and ulcerative and granulomatous colitis, isolated polyps, and inherited familial polyposis to carcinoma of the colon.

The most common tumor of the colon is adenomatous polyp. Primary lymphoma is rare in the colon and most common in the small intestine.

Adenomatous polyps are the most common benign gastrointestinal tumors. They occur throughout the GI tract, most commonly in the colon and stomach, and are found more frequently in males than in females. They may be single, or more commonly, multiple, and sessile or pedunculated. They may be inherited, as in familial polyposis and Gardener's syndrome, which primarily involves the colon. Development of colon cancer is common in familial polyposis. Polyps often cause bleeding, which may occult or gross, but rarely cause pain unless complications ensue. Papillary adenoma, a less common form found only in the colon, may also cause electrolyte loss and mucoid discharge.

A malignant tumor includes a carcinoma of the colon which may be infiltrating or exophytic and occurs most commonly in the rectosigmoid. Because the content of the ascending colon is liquid, a carcinoma in this area usually does not cause obstruction, but the patient tends to be to present late in the course of the disease with anemia, abdominal pain, or an abdominal mass or a palpable mass.

The prognosis with colonic tumors depends on the degree of bowel wall invasion and on the presence of regional lymph node involvement and distant metastases. The prognosis with carcinoma of the rectum and descending colon is quite unexpectedly good. Cure rates of 80 to 90% are possible with early resection before nodal invasion develops. For this reason, great care must be taken to exclude this disease when unexplained anemia, occult gastrointestinal bleeding, or change in bowel habits develop in a previously healthy patient. Complete removal of the lesion before it spreads to the lymph nodes provides the best chance of survival for a patient with cancer of the colon. Detection in an asymptotic patient by occult-bleeding, blood screening results in the highest five year survival.

Clinically suspected malignant lesions can usually be detected radiologically. Polyps less than 1 cm can easily be missed, especially in the upper sigmoid and in the presence of diverticulosis. Clinically suspected and radiologically detected lesions in the esophagus, stomach or colon can be confirmed by fiber optic endoscopy combined with histologic tissue diagnosis made by directed biopsy and brush sitology. Colonoscopy is another method utilized to detect colon diseases. Benign and malignant polyps not visualized by X-ray are often detected on colonoscopy. In addition, patients with one lesion on X-ray often have additional lesions detected on colonoscopy. Sigmoidoscope examination, however, only detects about 50% of colonic tumors.

The above methods of detecting colon cancer have drawbacks, for example, small colonic tumors may be missed by all of the above-described methods. The importance of detecting colon cancer is also extremely important to prevent metastases.

In accordance with an aspect of the present invention, there are provided nucleic acid probes comprising nucleic acid molecules of sufficient length to specifically hybridize to the RNA transcribed from the human colon specific genes of the present invention or to DNA corresponding to such RNA.

In accordance with another aspect of the present invention there is provided a method of and products for diagnosing colon cancer metastases by detecting the presence of RNA transcribed from the human colon specific genes of the present invention or DNA corresponding to such RNA in a sample derived from a host.

In accordance with yet another aspect of the present invention, there is provided a method of and products for diagnosing colon cancer metastases by detecting an altered level of a polypeptide corresponding to the colon specific genes of the present invention in a sample derived from a host, whereby an elevated level of the polypeptide indicates a colon cancer diagnosis.

In accordance with another aspect of the present invention, there are provided isolated polynucleotides encoding human colon specific polypeptides, including mRNAs, DNAs, cDNAs, genomic DNAs, as well as antisense analogs and biologically active and diagnostically or therapeutically useful fragments thereof.

In accordance with still another aspect of the present invention there are provided human colon specific genes which include polynucleotides as set forth in the sequence listing.

In accordance with a further aspect of the present invention, there are provided novel polypeptides encoded by the polynucleotides, as well as biologically active and diagnostically or therapeutically useful fragments, analogs and derivatives thereof.

In accordance with yet a further aspect of the present invention, there is provided a process for producing such polypeptides by recombinant techniques comprising culturing recombinant prokaryotic and/or eukaryotic host cells, containing a polynucleotide of the present invention, under conditions promoting expression of said proteins and subsequent recovery of said proteins.

In accordance with yet a further aspect of the present invention, there are provided antibodies specific to such polypeptides.

In accordance with another aspect of the present invention, there are provided processes for using one or more of the polypeptides of the present invention to treat colon cancer and for using the polypeptides to screen for compounds which interact with the polypeptides, for example, compounds which inhibit or activate the polypeptides of the present invention.

In accordance with yet another aspect of the present invention, there are provided compounds which inhibit activation of one or more of the polypeptides of the present invention which may be used to therapeutically, for example, in the treatment of colon cancer.

In accordance with yet a further aspect of the present invention, there are provided processes for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 is a partial cDNA sequence and the corresponding deduced amino acid sequence of a colon specific gene of the present invention.

FIG. 2 is a partial cDNA sequence and the corresponding deduced amino acid sequence of a colon specific gene of the present invention.

FIG. 3 is a partial cDNA sequence of a colon specific gene of the present invention.

FIG. 4 is a partial cDNA sequence and the corresponding deduced amino acid sequence of a colon specific gene of the present invention.

FIG. 5 is a partial cDNA sequence and the corresponding deduced amino acid sequence of a colon specific gene of the present invention.

FIG. 6 is a partial cDNA sequence and the corresponding deduced amino acid sequence of a colon specific gene of the present invention.

FIG. 7 is a partial cDNA sequence a colon specific gene of the present invention.

FIG. 8 is a full length cDNA sequence and the corresponding deduced amino acid sequence of a colon specific gene of the present invention.

FIG. 9 is a full length cDNA sequence and corresponding deduced amino acid sequence of a colon specific gene of the present invention.

FIG. 10 is a partial cDNA sequence and corresponding deduced amino acid sequence of a colon specific gene of the present invention.

FIG. 11 is a partial cDNA sequence and the corresponding deduced amino acid sequence of a colon specific gene of the present invention.

FIG. 12 is a partial cDNA sequence of a colon specific gene of the present invention.

FIG. 13 is a partial cDNA sequence of a colon specific gene of the present invention.

The term "colon specific gene" means that such gene is primarily expressed in tissues derived from the colon, and such genes may be expressed in cells derived from tissues other than from the colon. However, the expression of such genes is significantly higher in tissues derived from the colon than from non-colon tissues.

In accordance with one aspect of the present invention there is provided a polynucleotide which encodes one of the mature polypeptides having the deduced amino acid sequence of FIG. 8 or 9 and fragments, analogues and derivatives thereof.

In accordance with a further aspect of the present invention there is provided a polynucleotide which encodes the same mature polypeptide as a human gene having a coding portion which contains a polynucleotide which is at least 90% identical (preferably at least 95% identical and most preferably at least 97% or 100% identical) to one of the polynucleotides of FIGS. 1–7 or 9–13, as well as fragments thereof.

In accordance with still another aspect of the present invention there is provided a polynucleotide which encodes for the same mature polypeptide as a human gene whose coding portion includes a polynucleotide which is at least 90% identical to (preferably at least 95% identical to and most preferably at least 97% or 100% identical) to one of the polynucleotides included in ATCC Deposit No. 97,102 deposited Mar. 20, 1995.

The ATCC number referred to above is directed to a biological deposit with the ATCC, 12301 Parklawn Drive, Rockville, Md. 20852. Since the strain referred to is being maintained under the terms of the Budapest Treaty, it will be made available to a patent office signatory to the Budapest Treaty.

In accordance with yet another aspect of the present invention, there is provided a polynucleotide probe which hybridizes to mRNA (or the corresponding cDNA) which is transcribed from the coding portion of a human gene which coding portion includes a DNA sequence which is at least 90% identical to (preferably at least 95% identical to) and most preferably at least 97% or 100% identical) to one of the polynucleotide sequences of FIGS. 1–13.

The present invention further relates to a mature polypeptide encoded by a coding portion of a human gene which coding portion include a DNA sequence which is at lest 90% identical to (preferably at least 95% identical to and more preferably 97% or 100% identical to) one of the polynucleotides of FIGS. 1–7 or 10–13, as well as analogues, derivatives and fragments of such polypeptides.

The present invention also relates to one of the mature polypeptides of FIGS. 8 or 9 and fragments, analogues and derivatives of such polypeptides.

The present invention further relates to the same mature polypeptide encoded by a human gene whose coding portion includes DNA which is at least 90% identical to (preferably at least 95% identical to and more preferably at least 97% or 100% identical to) one of the polynucleotides included in ATCC Deposit No. 97,102 deposited Mar. 20, 1995.

In accordance with an aspect of the present invention, there are provided isolated nucleic acids (polynucleotides) which encode for the mature polypeptides having the deduced amino acid sequence of FIGS. 8 or 9 or fragments, analogues or derivatives thereof.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may include DNA identical to FIGS. 1–13 or that of the deposited clone or may be a different coding sequence which coding sequence, as a result of the redundancy or degeneracy of the genetic code, encodes the same mature polypeptide as the coding sequence of a gene which coding sequence includes the DNA of FIGS. 1–13 or the deposited cDNA.

The polynucleotide which encodes a mature polypeptide of the present invention may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode fragments, analogs and derivatives of a mature polypeptide of the present invention. The variant of the polynucleotide may be a naturally occurring allelic variant of the polynucleotide or a non-naturally occurring variant of the polynucleotide.

Thus, the present invention includes polynucleotides encoding the same mature polypeptide as hereinabove described as well as variants of such polynucleotides which variants encode a fragment, derivative or analog of a polypeptide of the invention. Such nucleotide variants include deletion variants, substitution variants and addition or insertion variants.

The polynucleotides of the invention may have a coding sequence which is a naturally occurring allelic variant of the human gene whose coding sequence includes DNA as shown in FIGS. 1–13 or of the coding sequence of the DNA in the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode a mature protein, or a protein having a prosequence of a protein having both a presequence and a presequence (leader sequence).

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, L. et al., Cell, 37:767 (1984)).

The present invention further relates to polynucleotides which hybridize to the hereinabove-described polynucleotides if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide of the present invention encoded by a coding sequence which includes the DNA of FIGS. 1–13 or the deposited cDNA(s).

Alternatively, the polynucleotide may have at least 10 or 20 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for polynucleotides, for example, for recovery of the polynucleotide or as a diagnostic probe or as a PCR primer.

Thus, the present invention is directed to polynucleotides having at least a 70% identity, preferably at least 90% and more preferably at least 95% identity to a polynucleotide which encodes the mature polypeptide encoded by a human gene which includes the DNA of one of FIGS. 1–13 as well as fragments thereof, which fragments have at least 30 bases and preferably at least 50 bases and to polypeptides encoded by such polynucleotides.

The partial sequences are specific tags for messenger RNA molecules. The complete sequence of that messenger RNA, in the form of cDNA, can be determined using the partial sequence as a probe to identify a cDNA clone corresponding to a full-length transcript, followed by sequencing of that clone. The partial cDNA clone can also be used as a probe to identify a genomic clone or clones that contain the complete gene including regulatory and promoter regions, exons, and introns.

The partial sequences of FIGS. 1–7 and 10–13 may be used to identify the corresponding full length gene from which they were derived. The partial sequences can be nick-translated or end-labelled with $^{32}P$ using polynucleotide kinase using labelling methods known to those with skill in the art (Basic Methods in Molecular Biology, L. G. Davis, M. D. Dibner, and J. F. Battey, ed., Elsevier Press, N.Y., 1986). A lambda library prepared from human colon tissue can be directly screened with the labelled sequences of interest or the library can be converted en masse to pBluescript (Stratagene Cloning Systems, La Jolla, Calif. 92037) to facilitate bacterial colony screening. Regarding pBluescript, see Sambrook et al., Molecular Cloning-A Laboratory Manual, Cold Spring Harbor Laboratory Press (1989), pg. 1.20. Both methods are well known in the art.

Briefly, filters with bacterial colonies containing the library in pBluescript or bacterial lawns containing lambda plaques are denatured and the DNA is fixed to the filters. The filters are hybridized with the labelled probe using hybridization conditions described by Davis et al., supra. The partial sequences, cloned into lambda or pBluescript, can be used as positive controls to assess background binding and to adjust the hybridization and washing stringencies necessary for accurate clone identification. The resulting autoradiograms are compared to duplicate plates of colonies or plaques; each exposed spot corresponds to a positive colony or plaque. The colonies or plaques are selected, expanded and the DNA is isolated from the colonies for further analysis and sequencing.

Positive cDNA clones are analyzed to determine the amount of additional sequence they contain using PCR with one primer from the partial sequence and the other primer from the vector. Clones with a larger vector-insert PCR product than the original partial sequence are analyzed by restriction digestion and DNA sequencing to determine whether they contain an insert of the same size or similar as the mRNA size determined from Northern blot Analysis.

Once one or more overlapping cDNA clones are identified, the complete sequence of the clones can be determined. The preferred method is to use exonuclease. III digestion (McCombie, W. R., Kirkness, E., Fleming, J. T., Kerlavage, A. R., Iovannisci, D. M., and Martin-Gallardo, R., Methods, 3:33–40, 1991). A series of deletion clones are generated, each of which is sequenced. The resulting overlapping sequences are assembled into a single contiguous sequence of high redundancy (usually three to five overlapping sequences at each nucleotide position), resulting in a highly accurate final sequence.

The DNA sequences (as well as the corresponding RNA sequences) also include sequences which are or contain a DNA sequence identical to one contained in and isolatable from ATCC Deposit No. 97102, deposited Mar. 20, 1995, and fragments or portions of the isolated DNA sequences (and corresponding RNA sequences), as well as DNA (RNA) sequences encoding the same polypeptide.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to polynucleotides which have at least 10 bases, preferably at least 20 bases, and may have 30 or more bases, which polynucleotides are hybridizable to and have at least a 70% identity to RNA (and DNA which corresponds to such RNA) transcribed from a human gene whose coding portion includes DNA as hereinabove described.

Thus, the polynucleotide sequences which hybridize as described above may be used to hybridize to and detect the expression of the human genes to which they correspond for use in diagnostic assays as hereinafter described.

In accordance with still another aspect of the present invention there are provided diagnostic assays for detecting micrometastases of colon cancer in a host. While applicant does not wish to limit the reasoning of the present invention to any specific scientific theory, it is believed that the presence of active transcription of a colon specific gene of the present invention in cells of the host, other than those derived from the colon, is indicative of colon cancer metastases. This is true because, while the colon specific genes are found in all cells of the body, their transcription to mRNA, cDNA and expression products is primarily limited to the colon in non-diseased individuals. However, if colon cancer is present, colon cancer cells migrate from the cancer to other cells, such that these other cells are now actively transcribing and expressing a colon specific gene at a greater level than is normally found in non-diseased individuals, i.e., transcription is higher than found in non-colon tissues in healthy individuals. It is the detection of this enhanced transcription or enhanced protein expression in cells, other than those derived from the colon, which is indicative of metastases of colon cancer.

In one example of such a diagnostic assay, an RNA sequence in a sample derived from a tissue other than the colon is detected by hybridization to a probe. The sample contains a nucleic acid or a mixture of nucleic acids, at least one of which is suspected of containing a human colon specific gene or fragment thereof of the present invention which is transcribed and expressed in such tissue. Thus, for example, in a form of an assay for determining the presence of a specific RNA in cells, initially RNA is isolated from the cells.

A sample may be obtained from cells derived from tissue other than from the colon including but not limited to blood, urine, saliva, tissue biopsy and autopsy material. The use of such methods for detecting enhanced transcription to mRNA from a human colon specific gene of the present invention or fragment thereof in a sample obtained from cells derived from other than the colon is well within the scope of those skilled in the art from the teachings herein.

The isolation of mRNA comprises isolating total cellular RNA by disrupting a cell and performing differential centrifugation. Once the total RNA is isolated, mRNA is isolated by making use of the adenine nucleotide residues known to those skilled in the art as a poly(A) tail found on virtually every eukaryotic mRNA molecule at the 3' end thereof. Oligonucleotides composed of only deoxythymidine [oligo(dT)] are linked to cellulose and the oligo(dT)-cellulose packed into small columns. When a preparation of total cellular RNA is passed through such a column, the mRNA molecules bind to the oligo(dT) by the poly(A)tails while the rest of the RNA flows through the column. The bound mRNAs are then eluted from the column and collected.

One example of detecting isolated mRNA transcribed from a colon specific gene of the present invention comprises screening the collected mRNAs with the gene specific oligonucleotide probes, as hereinabove described.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product.

An example of detecting a polynucleotide complementary to the mRNA sequence (cDNA) utilizes the polymerase chain reaction (PCR) in conjunction with reverse transcriptase. PCR is a very powerful method for the specific amplification of DNA or RNA stretches (Saiki et al., Nature, 234:163–166 (1986)). One application of this technology is in nucleic acid probe technology to bring up nucleic acid sequences present in low copy numbers to a detectable level. Numerous diagnostic and scientific applications of this method have been described by H. A. Erlich (ed.) in PCR Technology-Principles and Applications for DNA Amplification, Stockton Press, U.S.A., 1989, and by M. A. Inis (ed.) in PCR Protocols, Academic Press, San Diego, U.S.A., 1990.

RT-PCR is a combination of PCR with the reverse transcriptase enzyme. Reverse transcriptase is an enzyme which produces cDNA molecules from corresponding mRNA molecules. This is important since PCR amplifies nucleic acid molecules, particularly DNA, and this DNA may be produced from the mRNA isolated from a sample derived from the host.

A specific example of an RT-PCR diagnostic assay involves removing a sample from a tissue of a host. Such a sample will be from a tissue, other than the colon, for example, blood. Therefore, an example of such a diagnostic assay comprises whole blood gradient isolation of nucleated cells, total RNA extraction, RT-PCR of total RNA and agarose gel electrophoresis of PCR products. The PCR products comprise cDNA complementary to RNA transcribed from one or more colon specific genes of the present invention or fragments thereof. More particularly, a blood sample is obtained and the whole blood is combined with an equal volume of phosphate buffered saline, centrifuged and the lymphocyte and granulocyte layer is carefully aspirated and rediluted in phosphate buffered saline and centrifuged again. The supernate is discarded and the pellet containing nucleated cells is used for RNA extraction using the RNazole B method as described by the manufacturer (Tel-Test Inc., Friendswood, Tex.).

Oligonucleotide primers and probes are prepared with high specificity to the DNA sequences of the present invention. The probes are at least 10 base pairs in length, preferably at least 30 base pairs in length and most preferably at least 50 base pairs in length or more. The reverse transcriptase reaction and PCR amplification are performed sequentially without interruption. Taq polymerase is used during PCR and the PCR products are concentrated and the entire sample is run on a Tris-borate-EDTA agarose gel containing ethidium bromide.

Another aspect of the present invention relates to assays which detect the presence of an altered level of the expression products of the colon specific genes of the present invention. Thus, for example, such an assay involves detection of the polypeptides of the present invention or fragments thereof.

In accordance with another aspect of the present invention, there is provided a method of diagnosing a disorder of the colon, for example colon cancer, by determining altered levels of the colon specific polypeptides of the present invention in a biological sample, derived from tissue other than from the colon. Elevated levels of the colon specific polypeptides of the present invention, excluding CSG7 and CSG10, indicates active transcription and expression of the corresponding colon specific gene product. Assays used to detect levels of a colon specific gene polypeptide in a sample derived from a host are well-known to those skilled in the art and include radioimmunoassays, competitive-binding assays, Western blot analysis, ELISA assays and "sandwich" assays. A biological sample may include, but is not limited to, tissue extracts, cell samples or biological fluids, however, in accordance with the present invention, a biological sample specifically does not include tissue or cells of the colon.

An ELISA assay (Coligan, et al., Current Protocols in Immunology, 1(2), Chapter 6, 1991) initially comprises preparing an antibody specific to a colon specific polypeptide of the present invention, preferably a monoclonal antibody. In addition, a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g., a polystyrene dish, that binds the proteins in the sample. Any free protein binding sites on the dish are then covered by incubating with a non-specific protein, such as BSA. Next, the monoclonal antibody is incubated in the dish during which time the monoclonal antibodies attach to the colon specific polypeptide attached to the polystyrene dish. All unbound monoclonal antibody is washed out with buffer. The reporter antibody linked to horseradish peroxidase is now placed in the dish resulting in binding of the reporter antibody to any monoclonal antibody bound to the colon specific gene polypeptide. Unattached reporter antibody is then washed out. Peroxidase substrates are then added to the dish and the amount of color developed in a given time period is a measurement of the amount of the colon specific polypeptide present in a given volume of patient sample when compared against a standard curve.

A competition assay may be employed where antibodies specific to a colon specific polypeptide are attached to a solid support. The colon specific polypeptide is then labeled and the labeled polypeptide a sample derived from the host are passed over the solid support and the amount of label detected, for example, by liquid scintillation chromatography, can be correlated to a quantity of the colon specific polypeptide in the sample.

A "sandwich" assay is similar to an ELISA assay. In a "sandwich" assay, colon specific polypeptides are passed over a solid support and bind to antibody attached to the solid support. A second antibody is then bound to the colon specific polypeptide. A third antibody which is labeled and is specific to the second antibody, is then passed over the solid support and binds to the second antibody and an amount can then be quantified.

In alternative methods, labeled antibodies to a colon specific polypeptide are used. In a one-step assay, the target molecule, if it is present, is immobilized and incubated with a labeled antibody. The labeled antibody binds to the immobilized target molecule. After washing to remove the unbound molecules, the sample is assayed for the presence of the label. In a two-step assay, immobilized target molecule is incubated with an unlabeled antibody. The target molecule-labeled antibody complex, if present, is then bound to a second, labeled antibody that is specific for the unlabeled antibody. The sample is washed and assayed for the presence of the label.

The choice of marker used to label the antibodies will vary depending upon the application. However, the choice of marker is readily determinable to one skilled in the art. These labeled antibodies may be used in immunoassays as well as in histological applications to detect the presence of the proteins. The labeled antibodies may be polyclonal or monoclonal.

The presence of active transcription, which is greater than that normally found, of the colon specific genes in cells other than from the colon, by the presence of an altered level of mRNA, cDNA or expression products is an important indication of the presence of a colon cancer which has metastasized, since colon cancer cells are migrating from the colon into the general circulation. Accordingly, this phenomenon may have important clinical implications since the method of treating a localized, as opposed to a metastasized, tumor is entirely different.

The assays described above may also be used to test whether bone marrow preserved before chemotherapy is contaminated with micrometastases of a colon cancer cell. In the assay, blood cells from the bone marrow are isolated and treated as described above, this method allows one to determine whether preserved bone marrow is still suitable for transplantation after chemotherapy.

The present invention further relates to mature polypeptides as well as fragments, analogs and derivatives of such polypeptide.

The terms "fragment," "derivative" and "analog" when referring to the polypeptides encoded by the genes of the invention means a polypeptide which retains essentially the same biological function or activity as such polypeptide. Thus, an analog includes a proprotein which can be activated by cleavage of the proprotein portion to produce an active mature polypeptide.

The polypeptides of the present invention may be recombinant polypeptides, natural polypeptides or synthetic polypeptides, preferably recombinant polypeptides.

The fragment, derivative or analog of the polypeptides encoded by the genes of the invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptides of FIGS. 8 and 9 (in particular the mature polypeptides) as well as polypeptides which have at least 70% similarity (preferably at least a 70% identity) to the polypeptides of FIGS. 8 and 9 and more preferably at least a 90% similarity (more preferably at least a 90% identity) to the polypeptides of FIGS. 8 and 9 and still more preferably at least a 95% similarity (still more preferably at least 95% identity) to the polypeptides of FIGS. 8 and 9 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the colon specific genes. The culture conditions, such as temperature, pH and the like, are those previously used with the host cell selected for expression, and will be apparent to those of ordinarily skill in the art.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium;* fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pBSKS, pNH8A, pkrH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading frame with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The colon specific gene polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polynucleotides of the present invention may have the coding sequence fused in frame to a marker sequence which allows for purification of the polypeptide of the present invention. An example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host, e.g. COS-7 cells, is used. The HAtag corresponds to an epitope derived from the influenza hemagglutinin protein (Wilson, I., et al., Cell, 37:767 (1984)).

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

In accordance with another aspect of the present invention there are provided assays which may be used to screen for therapeutics to inhibit the action of the colon specific genes or colon specific proteins of the present invention, excluding CSG7 and CSG10. One assay takes advantage of the reductase function of these proteins. The present invention discloses methods for selecting a therapeutic which forms a complex with colon specific gene proteins with sufficient affinity to prevent their biological action. The methods include various assays, including competitive assays where the proteins are immobilized to a support, and are contacted with a natural substrate and a labeled therapeutic either simultaneously or in either consecutive order, and determining whether the therapeutic effectively competes with the natural substrate in a manner sufficient to prevent binding of the protein to its substrate.

In another embodiment, the substrate is immobilized to a support, and is contacted with both a labeled colon specific polypeptide and a therapeutic (or unlabeled proteins and a labeled therapeutic), and it is determined whether the amount of the colon specific polypeptide bound to the substrate is reduced in comparison to the assay without the therapeutic added. The colon specific polypeptide may be labeled with antibodies.

In another example of such a screening assay, there is provided a mammalian cell or membrane preparation expressing a colon specific polypeptide of the present invention incubated with elements which undergo simultaneous oxidation and reduction, for example hydrogen and oxygen which together form water, wherein the hydrogen could be labeled by radioactivity, e.g., tritium, in the presence of the compound to be screened under conditions favoring the oxidation reduction reaction where hydrogen and oxygen form water. The ability of the compound to enhance or block this interaction could then be measured.

Potential therapeutic compounds include antibodies and anti-idiotypic antibodies as described above, or in some cases, an oligonucleotide, which binds to the polypeptide.

Another example is an antisense construct prepared using antisense technology, which is directed to a colon specific polynucleotide to prevent transcription. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979); Cooney et al, Science, 241:456 (1988); and Dervan et al., Science, 251: 1360 (1991)), thereby preventing transcription and the production of a colon specific polynucleotide. The antisense RNA oligonucleotide hybridizes to the mRNA in vivo and blocks translation of the mRNA molecule into the colon specific genes polypeptide (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the colon specific polypeptides.

Another example is a small molecule which binds to and occupies the active site of the colon specific polypeptide thereby making the active site inaccessible to substrate such that normal biological activity is prevented. Examples of small molecules include but are not limited to small peptides or peptide-like molecules.

These compounds may be employed to treat colon cancer, since they interact with the function of colon specific polypeptides in a manner sufficient to inhibit natural function which is necessary for the viability of colon cancer cells. The compounds may be employed in a composition with a pharmaceutically acceptable carrier, e.g., as hereinafter described.

The compounds of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal, intra-anal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg bodyweight per day. In most cases, the dosage is from about 10 µg/kg to about 1 mg/kg body weight daily, taking into account the routes of administration, symptoms, etc.

The colon specific genes and compounds which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding a polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, arian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other, promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of a colon specific genes of the present invention as a diagnostic. For example, some diseases result from inherited defective genes. The colon specific genes, CSG7 and CSG10, for example, have been found to have a reduced expression in colon cancer cells as compared to that in normal cells. Further, the remaining colon specific genes of the present invention are overexpressed in colon cancer. Accordingly, a mutation in these genes allows a detection of colon disorders, for example, colon cancer. A mutation in a colon specific gene of the present invention at the DNA level may be detected by a variety of techniques. Nucleic acids used for diagnosis (genomic DNA, mRNA, etc.) may be obtained from a patient's cells, other than from the colon, such as from blood, urine, saliva, tissue biopsy and autopsy material. The genomic DNA may be used directly for detection or may be amplified enzymatically by using PCR (Saiki, et al., *Nature*, 324:163–166 (1986)) prior to analysis. RNA or cDNA may also be used for the same purpose. As an example, PCR primers complementary to the nucleic acid of the instant invention can be used to identify and analyze mutations in a colon specific polynucleotide of the present invention. For example, deletions and insertions can be detected by a change in size of the amplified product in comparison to the normal genotype. Point mutations can be identified by hybridizing amplified DNA to radiolabelled colon specific RNA or, alternatively, radiolabelled antisense DNA sequences.

Another well-established method for screening for mutations in particular segments of DNA after PCR amplification is single-strand conformation polymorphism (SSCP) analysis. PCR products are prepared for SSCP by ten cycles of reamplification to incorporate $^{32}$P-dCTP, digested with an appropriate restriction enzyme to generate 200–300 bp fragments, and denatured by heating to 85° C. for 5 min. and then plunged into ice. Electrophoresis is then carried out in a nondenaturing gel (5% glycerol, 5% acrylamide) (Glavac, D. and Dean, M., Human Mutation, 2:404–414 (1993)).

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotides or by automatic sequencing procedures with fluorescent-tags.

Genetic testing based on DNA sequence differences may be achieved by detection of alteration in electrophoretic mobility of DNA fragments and gels with or without denaturing agents. Small sequence deletions and insertions can be visualized by high-resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers, et al., Science, 230:1242 (1985)). In addition, sequence alterations, in particular small deletions, may be detected as changes in the migration pattern of DNA.

Sequence changes at specific locations may also be revealed by nuclease protection assays, such as Rnase and S1 protection or the chemical cleavage method (e.g., Cotton, et al., PNAS, U.S.A., 85:4397–4401 (1985)).

Thus, the detection of the specific DNA sequence may be achieved by methods such as hybridization, RNase protection, chemical cleavage, direct DNA sequencing, or the use of restriction enzymes (e.g., Restriction Fragment Length Polymorphisms (RFLP)) and Southern blotting.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Transgenic mice may also be used to generate antibodies.

The antibodies may also be employed to target colon cancer cells, for example, in a method of homing interaction agents which, when contacting colon cancer cells, destroy them. This is true since the antibodies are specific for the colon specific polypeptides of the present invention. A linking of the interaction agent to the antibody would cause the interaction agent to be carried directly to the colon.

Antibodies of this type may also be used to do in vivo imaging, for example, by labeling the antibodies to facilitate scanning of the pelvic area and the colon. One method for imaging comprises contacting any cancer cells of the colon to be imaged with an anti-colon specific protein-antibody labeled with a detectable marker. The method is performed under conditions such that the labeled antibody binds to the colon specific polypeptides. In a specific example, the antibodies interact with the colon, for example, colon cancer cells, and fluoresce upon contact such that imaging and visibility of the colon are enhanced to allow a determination of the diseased or non-diseased state of the colon.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Determination of Transcription of a colon specific gene

To assess the presence or absence of active transcription of a colon specific gene RNA, approximately 6 ml of venous blood is obtained with a standard venipuncture technique using heparinized tubes. Whole blood is mixed with an equal volume of phosphate buffered saline, which is then layered over 8 ml of Ficoll (Pharmacia, Uppsala, Sweden) in a 15-ml polystyrene tube. The gradient is centrifuged at 1800×g for 20 min at 5° C. The lymphocyte and granulocyte layer (approximately 5 ml) is carefully aspirated and rediluted up to 50 ml with phosphate-buffered saline in a 50-ml tube, which is centrifuged again at 1800×g for 20 min. at 5° C. The supernatant is discarded and the pellet containing nucleated cells is used for RNA extraction using the RNazole B method as described by the manufacturer (Tel-Test Inc., Friendswood, Tex.).

To determine the quantity of mRNA from the gene of interest, a probe is designed with an identity to at least portion of the mRNA sequence transcribed from a human gene whose coding portion includes a DNA sequence of one of FIGS. 1–13. This probe is mixed with the extracted RNA and the mixed DNA and RNA are precipitated with ethanol −70° C. for 15 minutes). The pellet is resuspended in hybridization buffer and dissolved. The tubes containing the mixture are incubated in a 72° C. water bath for 10–15 mins. to denature the DNA. The tubes are rapidly transferred to a water bath at the desired hybridization temperature. Hybridization temperature depends on the G+C content of the DNA. Hybridization is done for 3 hrs. 0.3 ml of nuclease-S1 buffer is added and mixed well. 50 µl of 4.0M ammonium acetate and 0.1M EDTA is added to stop the reaction. The mixture is extracted with phenol/chloroform and 20 µg of carrier tRNA is added and precipitation is done with an equal volume of isopropanol. The precipitate is dissolved in 40 µl of TE (pH 7.4) and run on an alkaline agarose gel. Following electrophoresis, the RNA is microsequenced to confirm the nucleotide sequence. (See Favaloro, J. et al., Methods Enzymol., 65:718 (1980) for a more detailed review).

Two oligonucleotide primers are employed to amplify the sequence isolated by the above methods. The 5' primer is 20 nucleotides long and the 3' primer is a complimentary sequence for the 3' end of the isolated mRNA. The primers are custom designed according to the isolated mRNA. The reverse transcriptase reaction and PCR amplification are performed sequentially without interruption in a Perkin Elmer 9600 PCR machine (Emeryville, Calif.). Four hundred ng total RNA in 20 µl diethylpyrocarbonate-treated water are placed in a 65° C. water bath for 5 min. and then quickly chilled on ice immediately prior to the addition of PCR reagents. The 50-µl total PCR volume consisted of 2.5 units Taq polymerase (Perkin-Elmer). 2 units arian myeloblastosis virus reverse transcriptase (Boehringer Mannheim, Indianapolis, Ind.); 200 µM each of dCTP, dATP, dGTP and dTTP (Perkin Elmer); 18 pM each primer, 10 mM Tris-HCl; 50 mM KCl; and 2 mM $MgCl_2$ (Perkin Elmer). PCR conditions are as follows: cycle 1 is 42° C. for 15 min then 97° C. for 15 s (1 cycle); cycle 2 is 95° C. for 1 min. 60° C.

for 1 min. and 72° C. for 30 s (15 cycles); cycle 3 is 95° C. for 1 min. 60° C. for 1 min., and 72° C. for 1 min. (10 cycles); cycle 4 is 95° C. for 1 min., 60° C. for 1 min., and 72° C. for 2 min. (8 cycles); cycle 5 is 72° C. for 15 min. (1 cycle); and the final cycle is a 4° C. hold until sample is taken out of the machine. The 50-μl PCR products are concentrated down to 10 μl with vacuum centrifugation, and a sample is then run on a thin 1.2% Tris-borate-EDTA agarose gel containing ethidium bromide. A band of expected size would indicate that this gene is present in the tissue assayed. The amount of RNA in the pellet may be quantified in numerous ways, for example, it may be weighed.

Verification of the nucleotide sequence of the PCR products is done by microsequencing. The PCR product is purified with a Qiagen PCR Product Purification Kit (Qiagen, Chatsworth, Calif.) as described by the manufacturer. One μg of the PCR product undergoes PCR sequencing by using the Taq DyeDeoxy Terminator Cycle sequencing kit in a Perkin-Elmer 9600 PCR machine as described by Applied Biosystems (Foster, Calif.). The sequenced product is purified using Centri-Sep columns (Princeton Separations, Adelphia, N.J.) as described by the company. This product is then analyzed with an ABI model 373A DNA sequencing system (Applied Biosystems) integrated with a Macintosh IIci computer.

EXAMPLE 2
Bacterial Expression and Purification of the CSG Proteins and Use For Preparing a Monoclonal Antibody The DNA sequence encoding a polypeptide of the present invention, ATCC #97102, which one is initially amplified using PCR oligonucleotide primers corresponding to the 5' sequences of the processed protein (minus the signal peptide sequence) and the vector sequences 3' to the gene. Additional nucleotides corresponding to the DNA sequence are added to the 5' and 3' sequences respectively. The 5' oligonucleotide primer may contain, for example, a restriction enzyme site followed by nucleotides of coding sequence starting from the presumed terminal amino acid of the processed protein. The 3' sequence may, for example, contain complementary sequences to a restriction enzyme site and also be followed by nucleotides of the nucleic acid sequence encoding the protein of interest. The restriction enzyme sites correspond to the restriction enzyme sites on a bacterial expression vector, for example, pQE-9 (Qiagen, Inc. Chatsworth, Calif.). pQE-9 encodes antibiotic resistance ($Amp^r$), a bacterial origin of replication (ori), an IPTG-regulatable promoter operator (P/O), a ribosome binding site (RBS), a 6-His tag and restriction enzyme sites. pQE-9 is then digested with the restriction enzymes corresponding to restriction enzyme sites contained in he primer sequences. The amplified sequences are ligated into pQE-9 and inserted in frame with the sequence encoding for the histidine tag and the RBS. The ligation mixture is then used to transform an *E. coli* strain, for example, M15/rep 4 (Qiagen) by the procedure described, in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized protein is purified from this solution by chromatography on a Nickel-Chelate column under conditions that allow for tight binding by proteins containing the 6-His tag (Hochuli, E. et al., J. Chromatography 411:177–184 (1984)). The protein is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

The protein purified in this manner may be used as an epitope to raise monoclonal antibodies specific to such protein. The monoclonal antibodies generated against the polypeptide the isolated protein can be obtained by direct injection of the polypeptides into an animal or by administering the polypeptides to an animal. The antibodies so obtained will then bind to the protein itself. Such antibodies can then be used to isolate the protein from tissue expressing that polypeptide by the use of an, for example, ELISA assay.

EXAMPLE 3
Preparation of cDNA Libraries from Colon Tissue

Total cellular RNA is prepared from tissues by the guanidinium-phenol method as previously described (P. Chomczynski and N. Sacchi, Anal. Biochem., 162: 156–159 (1987)) using RNAzol (Cinna-Biotecx). An additional ethanol precipitation of the RNA is included. Poly A mRNA is isolated from the total RNA using oligo dT-coated latex beads (Qiagen). Two rounds of poly A selection are performed to ensure better separation from non-polyadenylated material when sufficient quantities of total RNA are available.

The mRNA selected on the oligo dT is used for the synthesis of cDNA by a modification of the method of Gobbler and Hoffman (Gobbler, U. and B. J. Hoffman, 1983, Gene, 25:263). The first strand synthesis is performed using either Moloney murine sarcoma virus reverse transcriptase (Stratagene) or Superscript II (RNase H minus Moloney murine reverse transcriptase, Gibco-BRL). First strand synthesis is primed using a primer/linker containing an Xho I restriction site. The nucleotide mix used in the synthesis contains methylated dCTP to prevent restriction within the cDNA sequence. For second-strand synthesis *E. coli* polymerase Klenow fragment is used and [$^{32}$P]-dATP is incorporated as a tracer of nucleotide incorporation.

Following 2nd strand synthesis, the cDNA is made blunt ended using either T4 DNA polymerase or Klenow fragment. Eco RI adapters are added to the cDNA and the cDNA is restricted with Xho I. The cDNA is size fractionated over a Sephacryl S-500 column (Pharmacia) to remove excess linkers and cDNAs under approximately 500 base pairs.

The cDNA is cloned unidirectionally into the Eco RI-Xho I sites of either pBluescript II phagemid or lambda Uni-zap XR (Stratagene). In the case of cloning into pBluescript II, the plasmids are electroporated into *E. coli* SURE competent cells (Stratagene). When the cDNA is cloned into Uni-Zap XR it is packaged using the Gigipack II packaging extract (Stratagene). The packaged phage is used to infect SURE cells and amplified. The pBluescript phagemid containing the cDNA inserts are excised from the lambda Zap phage using the helper phage ExAssist (Stratagene). The rescued phagemid is plated on SOLR E. coli cells (Stratagene).

Preparation of Sequencing Templates

Template DNA for sequencing is prepared by 1) a boiling method or 2) PCR amplification.

The boiling method is a modification of the method of Holmes and Quigley (Holmes, D. S. and M. Quigley, 1981, Anal. Biochem., 114:193). Colonies from either cDNA cloned into Bluescript II or rescued Bluescript phagemid are grown in an enriched bacterial media overnight. 400 µl of cells are centrifuged and resuspended in STET (0.1M NaCl, 10 mM TRIS Ph 8.0, 1.0 mM EDTA and 5% Triton X-100) including lysozyme (80 µg/ml) and RNase A (4 µg/ml). Cells are boiled for 40 seconds and centrifuged for 10 minutes. The supernatant is removed and the DNA is precipitated with PEG/NaCl and washed with 70% ethanol (2×). Templates are resuspended in water at approximately 250 ng/µl.

Preparation of templates by PCR is a modification of the method of Rosenthal et al. (Rosenthal, et al., Nucleic Acids Res., 1993, 21:173–174). Colonies containing cDNA cloned into pBluescript II or rescued pBluescript phagemid are grown overnight in LB containing ampicillin in a 96 well tissue culture plate. Two µl of the cultures are used as template in a PCR reaction (Saiki, RK, et al., Science, 239:487–493, 1988; and Saiki, RK, et al., Science, 230:1350–1354, 1985) using a tricine buffer system (Ponce and Micol., Nucleic Acids Res., 1992, 20:1992.) and 200 µM dNTPs. The primer set chosen for amplification of the templates is outside of primer sites chosen for sequencing of the templates. The primers used are 5'-ATGCTTCCGGCTCGTATG-3' (SEQ ID NO:23) which is 5' of the M13 reverse sequence in pBluescript and 5'-GGGTTTTCCCAGTCACGAC-3', (SEQ ID NO:24) which is 3' of the M13 forward primer in pBluescript. Any primers which correspond to the sequence flanking the M13 forward and reverse sequences can be used. Perkin-Elmer 9600 thermocyclers are used for amplification of the templates with the following cycler conditions: 5 min at 94° C. (1 cycle); (20 sec at 94° C.); 20 sec at 55° C. (1 min at 72° C.) (30 cycles); 7 min at 72° C. (1 cycle). Following amplification the PCR templates are precipitated using PEG/NaCl and washed three times with 70% ethanol. The templates are resuspended in water.

EXAMPLE 4
Isolation of a Selected Clone From Colon Tissue

Two approaches are used to isolate a particular clone from a cDNA library prepared from human colon tissue.

In the first, a clone is isolated directly by screening the library using an oligonucleotide probe. To isolate a particular clone, a specific oligonucleotide with 30–40 nucleotides is synthesized using an Applied Biosystems DNA synthesizer according to one of the partial sequences described in this application. The oligonucleotide is labeled with $^{32}$P-ATP using T4 polynucleotide kinase and purified according to the standard protocol (Maniatis et al., Molecular Cloning: A Laboratory Manual, Cold Spring Harbor Press, Cold Spring, N.Y., 1982). The Lambda cDNA library is plated on 1.5% agar plate to a density of 20,000–550,000 pfu/150 mm plate. These plates are screened using Nylon membranes according to the standard phage screening protocol (Stratagene, 1993). Specifically, the Nylon membrane with denatured and fixed phage DNA is prehybridized in 6× SSC, 20 mM $NaH_2PO_4$, 0.4% SDS, 5× Denhardt's 500 µg/ml denatured, sonicated salmon sperm DNA; and 6× SSC, 0.1% SDS. After one hour of prehybridization, the membrane is hybridized with hybridization buffer 6× SSC, 20 mM $NaH_2PO_4$, 0.4% SDS, 500 µg/ml denatured, sonicated salmon sperm DNA with 1×10$^6$ cpm/ml $^{32}$P-probe overnight at 42° C. The membrane is washed at 45°–50° C. with washing buffer 6× SSC, 0.1% SDS for 20–30 minutes dried and exposed to Kodak X-ray film overnight. Positive clones are isolated and purified by secondary and tertiary screening. The purified clone sequenced to verify its identity to the partial sequence described in this application.

An alternative approach to screen the cDNA library prepared from human colon tissue is to prepare a DNA probe corresponding to the entire partial sequence. To prepare a probe, two oligonucleotide primers of 17–20 nucleotides derived from both ends of the partial sequence reported are synthesized and purified. These two oligonucleotides are used to amplify the probe using the cDNA library template. The DNA template is prepared from the phage lysate of the cDNA library according to the standard phage DNA preparation protocol (Maniatis et al.). The polymerase chain reaction is carried out in 25 µl reaction mixture with 0.5 µg of the above cDNA template. The reaction mixture is 1.5–5 mM $MgCl_2$, 0.01% (w/v) gelatin, 20 µM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with the Perkin-Elmer Cetus automated thermal cycler. The amplified product is analyzed by agarose gel electrophoresis and the DNA band with expected molecular weight is excised and purified. The PCR product is verified to be the probe by subcloning and sequencing the DNA product. The probe is labeled with the Multiprime DNA Labelling System (Amersham) at a specific activity <1×10$^9$ dmp/µg. This probe is used to screen the lambda cDNA library according to Stratagene's protocol. Hybridization is carried out with 5× TEN 920XTEN:0.3M Tris-HCl pH 8.0, 0.02M EDTA and 3M NaCl), 5× Denhardt's, 0.5% sodium pyrophosphate, 0.1% SDS, 0.2 mg/ml heat denatured salmon sperm DNA and 1×10$^6$ cpm/ml of [$^{32}$P]-labeled probe at 55° C. for 12 hours. The filters are washed in 0.5× TEN at room temperature for 20–30 min., then at 55° C. for 15 min. The filters are dried and autoradiographed at −70° C. using Kodak XAR-5 film. The positive clones are purified by secondary and tertiary screening. The sequence of the isolated clone are verified by DNA sequencing.

General procedures for obtaining complete sequences from partial sequences described herein are summarized as follows;

Procedure 1

Selected human DNA from the partial sequence clone (the cDNA clone that was sequenced to give the partial sequence) is purified e.g., by endonuclease digestion using Eco-R1, gel electrophoresis, and isolation of the clone by removal from low melting agarose gel. The isolated insert DNA, is radiolabeled e.g., with $^{32}$P labels, preferably by nick translation or random primer labeling. The labeled insert is used as a probe to screen a lambda phage cDNA library or a plasmid cDNA library. Colonies containing clones related to the probe cDNA are identified and purified by known purification methods. The ends of the newly purified clones are nucleotide sequenced to identify full length sequences. Complete sequencing of full length clones is then performed by Exonuclease III digestion or primer walking. Northern blots of the mRNA from various tissues using at least part of the deposited clone from which the partial sequence is obtained as a probe can optionally be performed to check the size of the mRNA against that of the purported full length cDNA.

The following procedures 2 and 3 can be used to obtain full length genes or full length coding portions of genes where a clone isolated from the deposited clone mixture does not contain a full length sequence. A library derived from human colon tissue or from the deposited clone mixture is also applicable to obtaining full length sequences from clones obtained from sources other than the deposited mixture by use of the partial sequences of the present invention.

Procedure 2
RACE Protocol For Recovery of Full-Length Genes

Partial cDNA clones can be made full-length by utilizing the rapid amplification of cDNA ends (RACE) procedure described in Frohman, M. A., Dush, M. K. and Martin, G. R. (1988) Proc. Nat'l. Acad. Sci. U.S.A., 85:8998-9002. A cDNA clone missing either the 5' or 3' end can be reconstructed to include the absent base pairs extending to the translational start or stop codon, respectively. In most cases, cDNAs are missing the start of translation therefor. The following briefly describes a modification of this original 5' RACE procedure. Poly A+ or total RNA is reverse transcribed with Superscript II (Gibco/BRL) and an antisense or complementary primer specific to the cDNA sequence. The primer is removed from the reaction with a Microcon Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoI, SalI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (Promega), restriction digested with XhoI or SalI, and ligated to a plasmid such as pBluescript SKII (Stratagene) at ShoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone.

Several quality-controlled kits are available for purchase. Similar reagents and methods to those above are supplied in kit form from Gibco/BRn. A second kit is available from Clontech which is a modification of a related technique, SLIC (single-stranded ligation to single-stranded cDNA) developed by Dumas et al. (Dumas, J. B., Edwards, M., Delort, J. and Mallet, Jr., 1991, Nucleic Acids Res., 19:5227-5232). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

Procedure 3
RNA Ligase Protocol For Generating The 5' End Sequences To Obtain Full Length Genes Once a gene of interest is identified, several methods are available for the identification of the 5' or 3' portions of the gene which may not be present in the original deposited clone. These methods include but are not limited to filter probing, clone enrichment using specific probes and protocols similar and identical to 5' and 3' RACE. While the full length gene may be present in a library and can be identified by probing, a useful method for generating the 5' end is to use the existing sequence information from the original partial sequence to generate the missing information. A method similar to 5' RACE is available for generating the missing 5' end of a desired full-length gene. (This method was published by Fromont-Racine et al, Nucleic Acids Res., 21(7):1683-1684 (1993). Briefly, a specific RNA oligonucleotide is ligated to the 5' ends of a population of RNA presumably containing full-length gene RNA transcript and a primer set containing a primer specific to the ligated RNA oligonucleotide. A primer specific to a known sequence (EST) of the gene of interest is used to PCR amplify the 5' portion of the desired full length gene which may then be sequenced and used to generate the full length gene. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap-cleaved RNA which can then be ligated to an RNA oligonucleotide using T4RNA ligase. This modified RNA preparation can then be used as a template for first strand cDNA synthesis using a gene-specific oligonucleotide. The first stand synthesis reaction can then be used as a template for PCR amplification of the desired 5' end using a primer specific to the ligated RNA oligonucleotide and a primer specific to the known sequence (EST) of the gene of interest. The resultant product is then sequenced and analyzed to confirm that the 5' end sequence belongs to the partial sequence.

EXAMPLE 5
Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

pMV-7 (Kirschmeier, P. T. et al, DNA, 7:219-25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagle's Medium (DMEM) with 10% calf serum (CS), penicillin and streptomycin. The mMSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide sequence selected from the group consisting of:

(a) a polynucleotide sequence having at least 95% identity to a polynucleotide sequence encoding a polypeptide consisting of amino acids 1 to 167 of SEQ ID NO:2;

(b) a polynucleotide sequence having at least 95% identity to a polynucleotide sequence encoding a polypeptide consisting of amino acids 2 to 135 of SEQ ID NO:7;

(c) a polynucleotide sequence having at least 95% identity to a polynucleotide sequence encoding a polypeptide consisting of amino acids 1 to 228 of SEQ ID NO:9;

(d) a polynucleotide sequence having at least 95% identity to a polynucleotide sequence encoding a polypeptide consisting of amino acids 1 to 163 of SEQ ID NO:11;

(e) a polynucleotide sequence having at least 95% identity to a polynucleotide sequence encoding a polypeptide consisting of amino acids 1 to 81 of SEQ ID NO:14;

(f) a polynucleotide sequence having at least 95% identity to a polynucleotide sequence encoding a polypeptide consisting of amino acids 2 to 323 of SEQ ID NO:16;

(g) a polynucleotide sequence having at least 95% identity to a polynucleotide sequence encoding a polypeptide consisting of amino acids 1 to 156 of SEQ ID NO:20; and (h) the complement of (a), (b), (c), (d), (e), (f) and (g).

2. The isolated polynucleotide of claim 1, wherein said member is (a), (b), (c), (d), (e), (f) or (g).

3. The isolated polynucleotide of claim 1 wherein said member is (b) and the polypeptide comprises amino acids 1 to 235 of SEQ ID No:7.

4. The isolated polynucleotide of claim 1 wherein said member is (f) and the polypeptide comprises amino acids 1 to 323 of SEQ ID No:16.

5. The isolated polynucleotide of claim 1 comprising a polynucleotide encoding a polypeptide member selected from the group consisting of:

(a) a polypeptide comprising the amino acid sequence identical to amino acids 1 to 167 of SEQ ID NO:2;

(b) a polypeptide comprising the amino acid sequence identical to amino acids 2 to 135 of SEQ ID NO:7;

(c) a polypeptide comprising the amino acid sequence identical to amino acids 1 to 228 of SEQ ID NO:9;

(d) a polypeptide comprising the amino acid sequence identical to amino acids 1 to 163 of SEQ ID NO:11;

(e) a polypeptide comprising the amino acid sequence identical to amino acids 1 to 81 of SEQ ID NO:14;

(f) a polypeptide comprising the amino acid sequence identical to amino acids 2 to 323 of SEQ ID NO:16; and (g) a polypeptide comprising the amino acid sequence identical to amino acids 1 to 156 of SEQ ID NO:20.

6. The isolated polynucleotide of claim 1 comprising a polynucleotide encoding a polypeptide member selected from the group consisting of:

(a) a polypeptide comprising the amino acid sequence identical to amino acids 1 to 135 of SEQ ID NO:7;

(b) a polypeptide comprising the amino acid sequence identical to amino acids 1 to 323 of SEQ ID NO:16.

7. The isolated polynucleotide of claim 1, wherein the polynucleotide is DNA.

8. The isolated polynucleotide of claim 1, wherein said polynucleotide is RNA.

9. A method of making a recombinant vector comprising inserting the isolated polynucleotide of claim 2 into a vector, wherein said polynucleotide is DNA.

10. A recombinant vector comprising the polynucleotide of claim 2, wherein said polynucleotide is DNA.

11. A recombinant host cell comprising the polynucleotide of claim 2, wherein said polynucleotide is DNA.

12. A method for producing a polypeptide comprising expressing from the recombinant cell of claim 11 the polypeptide encoded by said polynucleotide.

13. A process for producing a polypeptide comprising:
expressing from a recombinant cell containing the polynucleotide of claim 5 the polypeptide encoded by said polynucleotide.

14. A process for producing a polypeptide comprising:
expressing from a recombinant cell containing the polynucleotide of claim 6 the polypeptide encoded by said polynucleotide.

15. The isolated polynucleotide of claim 1, which is a member selected from the group consisting of:
 (a) a polynucleotide comprising nucleotides 1 to 501 of SEQ ID NO:1;
 (b) a polynucleotide comprising nucleotides 1 to 1209 of SEQ ID NO:5;
 (c) a polynucleotide comprising nucleotides 4 to 405 of SEQ ID NO:6;
 (d) a polynucleotide comprising nucleotides 2 to 685 of SEQ ID NO:8;
 (e) a polynucleotide comprising nucleotides 2 to 490 of SEQ ID NO:10;
 (f) a polynucleotide comprising nucleotides 1 to 709 of SEQ ID NO:12;
 (g) a polynucleotide comprising nucleotides 128 to 367 of SEQ ID NO:13;
 (h) a polynucleotide comprising nucleotides 45 to 1010 of SEQ ID NO:15; and
 ((i) a polynucleotide comprising nucleotides 2 to 469 of SEQ ID NO:19.

16. The isolated polynucleotide of claim 1, which is a member selected from the group consisting of:
 (a) a polynucleotide comprising nucleotides 1 to 405 of SEQ ID NO:6;
 (b) a polynucleotide comprising nucleotides 125 to 367 of SEQ ID NO:13; and
 (c) a polynucleotide comprising nucleotides 42 to 1010 of SEQ ID NO:15.

17. The isolated polynucleotide of claim 1, which is a member selected from the group consisting of:
 (a) a polynucleotide comprising the nucleotides of the sequence of SEQ ID NO:1;
 (b) a polynucleotide comprising the nucleotides of the sequence of SEQ ID NO:5;
 (c) a polynucleotide comprising the nucleotides of the sequence of SEQ ID NO:6;
 (d) a polynucleotide comprising the nucleotides of the sequence of SEQ ID NO:8;
 (e) a polynucleotide comprising the nucleotides of the sequence of SEQ ID NO:10;
 (f) a polynucleotide comprising the nucleotides of the sequence of SEQ ID NO:12;
 (g) a polynucleotide comprising the nucleotides of the sequence of SEQ ID NO:13;
 (h) a polynucleotide comprising the nucleotides of the sequence of SEQ ID NO:15; and
 (i) a polynucleotide comprising the nucleotides of the sequence of SEQ ID NO:19.

18. An isolated polynucleotide comprising a polynucleotide sequence selected from the group consisting of:
 (a) a polynucleotide sequence having at least a 95% identity to a polynucleotide sequence encoding a mature polypeptide encoded by the human cDNA in ATCC Deposit No. 97102; and
 (b) the complement of (a).

19. The isolated polynucleotide of claim 18, wherein the member is (a).

20. The isolated polynucleotide of claim 18, wherein said polynucleotide comprises DNA identical to a coding portion of the human cDNA in ATCC Deposit No. 97102 which encodes a mature polypeptide.

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 638 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: mat_peptide
        ( B ) LOCATION: 1..501

( i x ) FEATURE:
        ( A ) NAME/KEY: CDS
        ( B ) LOCATION: 1..501

( x i ) SEQUENCE DESCRIPTION: SEQ ID NO:1:

```
GCC  AGG  CAG  CTG  GCT  GCC  SAC  CAG  GCC  GTG  TAT  GTG  AAG  GTC  AAG  GCT        48
Ala  Arg  Gln  Leu  Ala  Ala  Xaa  Gln  Ala  Val  Tyr  Val  Lys  Val  Lys  Ala
 1              5                        10                       15

GAA  GCC  CGG  GAA  CTG  CTG  GGC  CAC  CCG  TGG  TCT  CTG  TGT  CCT  GTC  TGT        96
Glu  Ala  Arg  Glu  Leu  Leu  Gly  His  Pro  Trp  Ser  Leu  Cys  Pro  Val  Cys
                 20                       25                       30

GGG  TGC  CAA  CTC  ACC  ACC  TTT  GAT  GGG  GCC  CGT  GGT  GCC  ACC  ACT  CTC       144
Gly  Cys  Gln  Leu  Thr  Thr  Phe  Asp  Gly  Ala  Arg  Gly  Ala  Thr  Thr  Leu
         35                       40                       45

CTG  GTG  TCT  ATG  AAG  CTC  TCT  TCC  CGC  TGC  CCA  GGA  CTA  CAG  AAT  ACC       192
Leu  Val  Ser  Met  Lys  Leu  Ser  Ser  Arg  Cys  Pro  Gly  Leu  Gln  Asn  Thr
     50                       55                       60

ATC  CCC  TGG  TAC  CGT  GTA  GTT  GCC  GAA  GTC  CAG  ATC  TGC  CAT  GGC  AAA       240
Ile  Pro  Trp  Tyr  Arg  Val  Val  Ala  Glu  Val  Gln  Ile  Cys  His  Gly  Lys
 65                       70                       75                       80

ACG  GAG  GCT  GTG  GGC  CAG  GTC  CAC  ATC  TTC  TTC  CAG  GAT  GGG  ATG  GTG       288
Thr  Glu  Ala  Val  Gly  Gln  Val  His  Ile  Phe  Phe  Gln  Asp  Gly  Met  Val
                 85                       90                       95

ACG  TTG  ACT  CCA  AAC  AAG  GGT  GTG  TGG  GTG  AAT  GGT  CTC  CGA  GTG  GAT       336
```

```
Thr Leu Thr Pro Asn Lys Gly Val Trp Val Asn Gly Leu Arg Val Asp
            100             105             110

CTC CCA GCT GAG AAG TTA GCA TCT GTG TCC GTG AGT CGT ACA CCT GAT        384
Leu Pro Ala Glu Lys Leu Ala Ser Val Ser Val Ser Arg Thr Pro Asp
        115             120             125

GGC TCC CTG CTA GTC CGC CAG AAG GCA GGG GTC CAG GTG TGG CTT GGA        432
Gly Ser Leu Leu Val Arg Gln Lys Ala Gly Val Gln Val Trp Leu Gly
        130             135             140

GCC AAT GGG AAG GTG GCT GTG ATT GTG AGC AAT GAC CAT GCT GGG AAA        480
Ala Asn Gly Lys Val Ala Val Ile Val Ser Asn Asp His Ala Gly Lys
145             150             155             160

CTG TGT GGG GGC CTK TGG AAA ATTTGACGGG GGACCAGACC AATGATTGGG           531
Leu Cys Gly Gly Xaa Trp Lys
                165

ATGATTCCCA GGAGAAGCCA GCGATTGGGG AAWTGGAGAG CGCAGGGACT TTCT Y CCMCA    591

TGTTAATGGG CTTGWTCCAG TTCATCCCAC CAGGAACGAA GGATTTT                    638
```

( 2 ) INFORMATION FOR SEQ ID NO:2:

( i ) SEQUENCE CHARACTERISTICS:
        ( A ) LENGTH: 167 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ala Arg Gln Leu Ala Ala Xaa Gln Ala Val Tyr Val Lys Val Lys Ala
 1               5              10                  15

Glu Ala Arg Glu Leu Leu Gly His Pro Trp Ser Leu Cys Pro Val Cys
            20              25              30

Gly Cys Gln Leu Thr Thr Phe Asp Gly Ala Arg Gly Ala Thr Thr Leu
        35              40              45

Leu Val Ser Met Lys Leu Ser Ser Arg Cys Pro Gly Leu Gln Asn Thr
 50              55              60

Ile Pro Trp Tyr Arg Val Val Ala Glu Val Gln Ile Cys His Gly Lys
 65              70              75              80

Thr Glu Ala Val Gly Gln Val His Ile Phe Phe Gln Asp Gly Met Val
            85              90              95

Thr Leu Thr Pro Asn Lys Gly Val Trp Val Asn Gly Leu Arg Val Asp
            100             105             110

Leu Pro Ala Glu Lys Leu Ala Ser Val Ser Val Ser Arg Thr Pro Asp
        115             120             125

Gly Ser Leu Leu Val Arg Gln Lys Ala Gly Val Gln Val Trp Leu Gly
        130             135             140

Ala Asn Gly Lys Val Ala Val Ile Val Ser Asn Asp His Ala Gly Lys
145             150             155             160

Leu Cys Gly Gly Xaa Trp Lys
                165
```

( 2 ) INFORMATION FOR SEQ ID NO:3:

( i ) SEQUENCE CHARACTERISTICS:
        ( A ) LENGTH: 874 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:

(A) NAME/KEY: CDS
(B) LOCATION: 1..705

(ix) FEATURE:
(A) NAME/KEY: mat_peptide
(B) LOCATION: 1..705

(xi) SEQUENCE DESCRIPTION: SEQ ID NO:3:

| | | | | | | | | | | | | | | | | |
|---|---|---|---|---|---|---|---|---|---|---|---|---|---|---|---|---|
| CAG | GAC | TGC | GTG | TGC | ACG | GAC | AAG | GTG | GAC | AAC | AAC | ACC | CTG | CTC | AAC | 48 |
| Gln | Asp | Cys | Val | Cys | Thr | Asp | Lys | Val | Asp | Asn | Asn | Thr | Leu | Leu | Asn | |
| 1 | | | | 5 | | | | | 10 | | | | | 15 | | |
| GTC | ATC | GCC | TGC | ACC | CAC | GTG | CCC | TGC | AAC | ACC | TCC | TGC | AGC | CCT | GGG | 96 |
| Val | Ile | Ala | Cys | Thr | His | Val | Pro | Cys | Asn | Thr | Ser | Cys | Ser | Pro | Gly | |
| | | | 20 | | | | | 25 | | | | | 30 | | | |
| TTC | GAA | CTC | ATG | GAG | GCC | CCC | GGG | GAG | TGC | TGT | AAG | AAG | TGT | GAA | CAG | 144 |
| Phe | Glu | Leu | Met | Glu | Ala | Pro | Gly | Glu | Cys | Cys | Lys | Lys | Cys | Glu | Gln | |
| | | 35 | | | | | 40 | | | | | 45 | | | | |
| ACG | CAC | TGT | ATC | ATC | AAA | CGG | CCC | GAC | AAC | CAG | CAC | GTC | ATC | CTG | AAG | 192 |
| Thr | His | Cys | Ile | Ile | Lys | Arg | Pro | Asp | Asn | Gln | His | Val | Ile | Leu | Lys | |
| | 50 | | | | | 55 | | | | | 60 | | | | | |
| CCC | GGG | GAC | TTC | AAG | AGC | GAC | CCG | AAG | AAC | AAC | TGC | ACA | TTC | TTC | AGC | 240 |
| Pro | Gly | Asp | Phe | Lys | Ser | Asp | Pro | Lys | Asn | Asn | Cys | Thr | Phe | Phe | Ser | |
| 65 | | | | 70 | | | | | 75 | | | | | 80 | | |
| TGC | GTG | AAG | ATC | CAC | AAC | CAG | CTC | ATC | TCG | TCC | GTT | TCC | AAC | ATC | ACC | 288 |
| Cys | Val | Lys | Ile | His | Asn | Gln | Leu | Ile | Ser | Ser | Val | Ser | Asn | Ile | Thr | |
| | | | 85 | | | | | 90 | | | | | 95 | | | |
| TGC | CCC | AAC | TTT | GAT | GCC | AGC | ATT | TGC | ATC | CCG | GGC | TCC | ATC | ACA | TTC | 336 |
| Cys | Pro | Asn | Phe | Asp | Ala | Ser | Ile | Cys | Ile | Pro | Gly | Ser | Ile | Thr | Phe | |
| | | 100 | | | | | 105 | | | | | 110 | | | | |
| ATG | CCC | AAT | GGA | TGC | TGC | AAG | ACC | TGC | ACC | CCT | CGC | AAT | GAG | ACC | AGG | 384 |
| Met | Pro | Asn | Gly | Cys | Cys | Lys | Thr | Cys | Thr | Pro | Arg | Asn | Glu | Thr | Arg | |
| | 115 | | | | | 120 | | | | | 125 | | | | | |
| GTG | CCC | TGC | TCC | ACC | GTC | CCC | GTC | ACC | ACG | GAG | GTT | TCG | TAC | GCC | GGC | 432 |
| Val | Pro | Cys | Ser | Thr | Val | Pro | Val | Thr | Thr | Glu | Val | Ser | Tyr | Ala | Gly | |
| | 130 | | | | | 135 | | | | | 140 | | | | | |
| TGC | ACC | AAG | ACC | GTC | CTC | ATG | AAT | CAT | TGC | TCC | GGG | TCC | TGC | GGG | ACA | 480 |
| Cys | Thr | Lys | Thr | Val | Leu | Met | Asn | His | Cys | Ser | Gly | Ser | Cys | Gly | Thr | |
| 145 | | | | 150 | | | | | 155 | | | | | 160 | | |
| TTT | GTC | ATG | TAC | TCG | GCC | AAG | GCC | CAG | GCC | CTG | GAC | CAC | AGC | TGC | TCC | 528 |
| Phe | Val | Met | Tyr | Ser | Ala | Lys | Ala | Gln | Ala | Leu | Asp | His | Ser | Cys | Ser | |
| | | | 165 | | | | | 170 | | | | | 175 | | | |
| TGC | TGC | AAA | GAG | GAG | AAA | ACC | AGC | CAG | CGT | GAG | GTG | GTC | CTG | AGC | TGC | 576 |
| Cys | Cys | Lys | Glu | Glu | Lys | Thr | Ser | Gln | Arg | Glu | Val | Val | Leu | Ser | Cys | |
| | | | 180 | | | | | 185 | | | | | 190 | | | |
| CCC | AAT | GGC | GGC | TCG | CTG | ACA | CAC | ACC | TAC | ACC | CAC | ATC | GAG | AGC | TGC | 624 |
| Pro | Asn | Gly | Gly | Ser | Leu | Thr | His | Thr | Tyr | Thr | His | Ile | Glu | Ser | Cys | |
| | | 195 | | | | | 200 | | | | | 205 | | | | |
| CAG | TGC | CAG | GAC | ACC | GTC | TGC | GGG | CTC | CCC | ACC | GGC | ACC | TCC | CGC | CGG | 672 |
| Gln | Cys | Gln | Asp | Thr | Val | Cys | Gly | Leu | Pro | Thr | Gly | Thr | Ser | Arg | Arg | |
| | 210 | | | | | 215 | | | | | 220 | | | | | |
| GCC | CGG | CGT | TCC | CCT | AGG | CAT | CTG | GGG | AGC | GGG | TGAGCGGGT | | GGGCACAGCC | | | 725 |
| Ala | Arg | Arg | Ser | Pro | Arg | His | Leu | Gly | Ser | Gly | | | | | | |
| 225 | | | | 230 | | | | | 235 | | | | | | | |

CCTTCACTGC CCTCGACAGC TTTACCTCCC CCGGACCCTC TGAGCCTCCT AAGCTCGGCT    785

TCCTCTCTTC AGATATTTAT TGTCTGAGTT TTTGTTCAGT CCTTGCTTTC CAATAATAAA    845

CTCAGGGGGA CATGCAAAAA AAAAAAAA    874

(2) INFORMATION FOR SEQ ID NO:4:

(i) SEQUENCE CHARACTERISTICS:
(A) LENGTH: 235 amino acids (B) TYPE: amino acid
(D) TOPOLOGY: linear (ii) MOLECULE TYPE: protein (xi) SEQUENCE DESCRIPTION: SEQ ID NO:4:

| Gln | Asp | Cys | Val | Cys | Thr | Asp | Lys | Val | Asp | Asn | Asn | Thr | Leu | Leu | Asn |
|---|---|---|---|---|---|---|---|---|---|---|---|---|---|---|---|
| 1 | | | | 5 | | | | | 10 | | | | | 15 | |

| Val | Ile | Ala | Cys | Thr | His | Val | Pro | Cys | Asn | Thr | Ser | Cys | Ser | Pro | Gly |
|---|---|---|---|---|---|---|---|---|---|---|---|---|---|---|---|
| | | | 20 | | | | | 25 | | | | | 30 | | |

| Phe | Glu | Leu | Met | Glu | Ala | Pro | Gly | Glu | Cys | Cys | Lys | Lys | Cys | Glu | Gln |
|---|---|---|---|---|---|---|---|---|---|---|---|---|---|---|---|
| | | 35 | | | | | 40 | | | | 45 | | | | |

| Thr | His | Cys | Ile | Ile | Lys | Arg | Pro | Asp | Asn | Gln | His | Val | Ile | Leu | Lys |
|---|---|---|---|---|---|---|---|---|---|---|---|---|---|---|---|
| | 50 | | | | | 55 | | | | | 60 | | | | |

| Pro | Gly | Asp | Phe | Lys | Ser | Asp | Pro | Lys | Asn | Asn | Cys | Thr | Phe | Phe | Ser |
|---|---|---|---|---|---|---|---|---|---|---|---|---|---|---|---|
| 65 | | | | | 70 | | | | | 75 | | | | | 80 |

| Cys | Val | Lys | Ile | His | Asn | Gln | Leu | Ile | Ser | Ser | Val | Ser | Asn | Ile | Thr |
|---|---|---|---|---|---|---|---|---|---|---|---|---|---|---|---|
| | | | | 85 | | | | | 90 | | | | | 95 | |

| Cys | Pro | Asn | Phe | Asp | Ala | Ser | Ile | Cys | Ile | Pro | Gly | Ser | Ile | Thr | Phe |
|---|---|---|---|---|---|---|---|---|---|---|---|---|---|---|---|
| | | | 100 | | | | | 105 | | | | | 110 | | |

| Met | Pro | Asn | Gly | Cys | Cys | Lys | Thr | Cys | Thr | Pro | Arg | Asn | Glu | Thr | Arg |
|---|---|---|---|---|---|---|---|---|---|---|---|---|---|---|---|
| | | 115 | | | | | 120 | | | | | 125 | | | |

| Val | Pro | Cys | Ser | Thr | Val | Pro | Val | Thr | Thr | Glu | Val | Ser | Tyr | Ala | Gly |
|---|---|---|---|---|---|---|---|---|---|---|---|---|---|---|---|
| | 130 | | | | | 135 | | | | | 140 | | | | |

| Cys | Thr | Lys | Thr | Val | Leu | Met | Asn | His | Cys | Ser | Gly | Ser | Cys | Gly | Thr |
|---|---|---|---|---|---|---|---|---|---|---|---|---|---|---|---|
| 145 | | | | | 150 | | | | | 155 | | | | | 160 |

| Phe | Val | Met | Tyr | Ser | Ala | Lys | Ala | Gln | Ala | Leu | Asp | His | Ser | Cys | Ser |
|---|---|---|---|---|---|---|---|---|---|---|---|---|---|---|---|
| | | | | 165 | | | | | 170 | | | | | 175 | |

| Cys | Cys | Lys | Glu | Glu | Lys | Thr | Ser | Gln | Arg | Glu | Val | Val | Leu | Ser | Cys |
|---|---|---|---|---|---|---|---|---|---|---|---|---|---|---|---|
| | | | 180 | | | | | 185 | | | | | 190 | | |

| Pro | Asn | Gly | Gly | Ser | Leu | Thr | His | Thr | Tyr | Thr | His | Ile | Glu | Ser | Cys |
|---|---|---|---|---|---|---|---|---|---|---|---|---|---|---|---|
| | | 195 | | | | | 200 | | | | | 205 | | | |

| Gln | Cys | Gln | Asp | Thr | Val | Cys | Gly | Leu | Pro | Thr | Gly | Thr | Ser | Arg | Arg |
|---|---|---|---|---|---|---|---|---|---|---|---|---|---|---|---|
| | 210 | | | | | 215 | | | | | 220 | | | | |

| Ala | Arg | Arg | Ser | Pro | Arg | His | Leu | Gly | Ser | Gly |
|---|---|---|---|---|---|---|---|---|---|---|
| 225 | | | | | 230 | | | | | 235 |

(2) INFORMATION FOR SEQ ID NO:5:

(i) SEQUENCE CHARACTERISTICS:
(A) LENGTH: 1209 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:5:

```
ATTGGTGCTA CCTGGCTCTC CTGTCTCTGC AGCTCTACAG GTGAGGCCCA GCAGAGGGAG      60
TAGGGCTCGC CATGTTTCTG GTGAGCCAAT TGGCTGATC  TTGGGTGTCT GAACAGCTAT     120
TGGGTCCACC CCAGTCCCTT TCAGCTGCTG CTTAATGCCC TGCTCTCTCC CTGGCCCACC     180
TTATAGAGAG CCCAAAGAGC TCCTGTAAGA GGGAGAACTC TATCTGTGGT TTATAATCTT     240
GCACGAGGCA CCAGAAGTCT CCCTGGGTCT TGTGAATGAA CTACATTTAT CCCCTTTCCT     300
GCCCCAACCA CAAACTCTTT CCTTCAAAGA GGGCCTGCCT GGTTCCCTCC ACCCAACTGC     360
ACCATGAGAT CGGTCCAAGA GTCCATTCCC CAGGTGGGAG CCAACTGTCA GGGAGGTCTT     420
TCCCACCAAA CATCTTTCAG TTGCTGGGAG GTGACCATAG GGCTCTGCTT TTAAAGATAT     480
```

```
GGCTGCTTCA AAGGCCAGAG TCACAGGAAG GACTTCTTCC AGGGAGATTA GTGGTGATGG      540

AGAGGAGAGT TAAAATGACC TCATGTCCTT CTTGTCCACG GTTTTGTTGA GTTTTCACTC      600

TTCTAATGCA AGGGTCTCAC ACTGTGAACC ACTTAGGATG TGATCACTTT CAGGTGGCCA      660

GGAATGTTGA ATGTCTTTGG CTCAGTTCAT CTAAAAAGA  TATCTATTTG AAAGTTCTCA      720

GAGTTGTACA TATGTTTCAC AGTACAGGAT CTGTACATAA AAGTTTCTTT CCTAAACCAT      780

TCACCAAGAG CCAATATCTA GGCATTTCCT CGGTAGCACA AATTTTCTNA TTGCTTAGAA      840

AATTGTCCTC CCTGTTCTTT CTGTCTGNAG ACTTAAGTGA GTTAGGTCTT TAAGGAAAGC      900

AACGCTCCTC TGAAATGCTT GTCTTTTTTC TGTTGCCGAA ATAGCTGGTC CTTTTCGGG       960

AGTTAGATGT ATAGAGTGTT TGTATGTAAA CATTTCTTGT AGGCATCACC ATGAACANAG     1020

ATATATTTTC TATTTANTTA NTATATGTGC ACTTCAAGAA GTCACTGTCA GAGAAATAAA     1080

GAATTGTCTT AAATGTCATG ATTGGAGATG TCCTTTGCAT TGCTTGGAAG GGGTGTACCT     1140

AGAGCCAAGG AAATTGGCTC TGGTTTGGAA AAATTTTGCT GTTATTATAG TAAACATACA     1200

AAGGATGTC                                                            1209
```

(2) INFORMATION FOR SEQ ID NO:6:

(i) SEQUENCE CHARACTERISTICS:
      (A) LENGTH: 548 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..405

(ix) FEATURE:
      (A) NAME/KEY: mat_peptide
      (B) LOCATION: 1..405

(xi) SEQUENCE DESCRIPTION: SEQ ID NO:6:

```
ATG AGT CCT GTG AAA AAC AAT GTG GGC AGA GGC CTA AAC ATC GCC CTG       48
Met Ser Pro Val Lys Asn Asn Val Gly Arg Gly Leu Asn Ile Ala Leu
 1               5                  10                  15

GTG AAT GGA ACC ACG GGA GCT GTG CTG GGA CAG AAG GCA TTT GAC ATG       96
Val Asn Gly Thr Thr Gly Ala Val Leu Gly Gln Lys Ala Phe Asp Met
         20                  25                  30

TAC TCT GGA GAT GTT ATG CAC CTA GTG AAA TTC CTT AAA GAA ATT CCG      144
Tyr Ser Gly Asp Val Met His Leu Val Lys Phe Leu Lys Glu Ile Pro
             35                  40                  45

GGG GGT GCA CTG GTG CTG GTG GCC TCC TAC GAC GAT CCA GGG ACC AAA      192
Gly Gly Ala Leu Val Leu Val Ala Ser Tyr Asp Asp Pro Gly Thr Lys
 50                  55                  60

ATG AAC GAT GAA AGC AGG AAA CTC TTC TCT GAC TTG GGG AGT TCC TAC      240
Met Asn Asp Glu Ser Arg Lys Leu Phe Ser Asp Leu Gly Ser Ser Tyr
 65                  70                  75                  80

GCA AAA CAA CTG GGC TTC CGG GAC AGC TGG GTC TTC ATA GGA GCC AAA      288
Ala Lys Gln Leu Gly Phe Arg Asp Ser Trp Val Phe Ile Gly Ala Lys
             85                  90                  95

GAC CTC AGG GGT AAA AGC CCC TTT GAG CAG TTC TTA AAG AAC AGC CCA      336
Asp Leu Arg Gly Lys Ser Pro Phe Glu Gln Phe Leu Lys Asn Ser Pro
                 100                 105                 110

GAC ACA AAC AAA TAC GAG GGA TGG CCA GAG CTG CTG GAG ATG GAG GGC      384
Asp Thr Asn Lys Tyr Glu Gly Trp Pro Glu Leu Leu Glu Met Glu Gly
            115                 120                 125
```

```
TGC ATG CCC CCG AAG CCA TTT TAGGGTGGCT GTGGCTCTTC CTCAGCCAGG          435
Cys Met Pro Pro Lys Pro Phe
    130             135

GGCCTGAAGA AG Y TCCTGCC TGCATTAGGA GTCANAGCCC GGCAGGCTGN AGGAGGAGGA   495

GCAGGGGGTG CTGCGTGGAA GGTGCTGCAG GCCTTGCACG CTGTGTCGCG CCT            548
```

( 2 ) INFORMATION FOR SEQ ID NO:7:

( i ) SEQUENCE CHARACTERISTICS:
        ( A ) LENGTH: 135 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Ser Pro Val Lys Asn Asn Val Gly Arg Gly Leu Asn Ile Ala Leu
1           5                   10                  15

Val Asn Gly Thr Thr Gly Ala Val Leu Gly Gln Lys Ala Phe Asp Met
            20                  25                  30

Tyr Ser Gly Asp Val Met His Leu Val Lys Phe Leu Lys Glu Ile Pro
        35              40                  45

Gly Gly Ala Leu Val Leu Val Ala Ser Tyr Asp Asp Pro Gly Thr Lys
    50              55                  60

Met Asn Asp Glu Ser Arg Lys Leu Phe Ser Asp Leu Gly Ser Ser Tyr
65              70                  75                      80

Ala Lys Gln Leu Gly Phe Arg Asp Ser Trp Val Phe Ile Gly Ala Lys
                85                  90                  95

Asp Leu Arg Gly Lys Ser Pro Phe Glu Gln Phe Leu Lys Asn Ser Pro
            100                 105                 110

Asp Thr Asn Lys Tyr Glu Gly Trp Pro Glu Leu Leu Glu Met Glu Gly
            115                 120                 125

Cys Met Pro Pro Lys Pro Phe
    130             135
```

( 2 ) INFORMATION FOR SEQ ID NO:8:

( i ) SEQUENCE CHARACTERISTICS:
        ( A ) LENGTH: 878 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..685

( x i ) SEQUENCE DESCRIPTION: SEQ ID NO:8:

```
T GTC TAC TCA AGG TAT TTC ACA ACT TAT GAC ACG AAT GGT AGA TAC        46
  Val Tyr Ser Arg Tyr Phe Thr Thr Tyr Asp Thr Asn Gly Arg Tyr
  1           5                   10                  15

AGT GTA AAA GTG CGG GCT CTG GGA GGA GTT AAC GCA GCC AGA CGG AGA      94
Ser Val Lys Val Arg Ala Leu Gly Gly Val Asn Ala Ala Arg Arg Arg
            20                  25                  30

GTG ATA CCC CAG CAG AGT GGA GCA CTG TAC ATA CCT GGC TGG ATT GAG      142
Val Ile Pro Gln Gln Ser Gly Ala Leu Tyr Ile Pro Gly Trp Ile Glu
            35                  40                  45

AAT GAT GAA ATA CAA TGG AAT CCA CCA AGA CCT GAA ATT AAT AAG GAT      190
Asn Asp Glu Ile Gln Trp Asn Pro Pro Arg Pro Glu Ile Asn Lys Asp
            50                  55                  60
```

| | | | | | | | | | | | | | | | |
|---|---|---|---|---|---|---|---|---|---|---|---|---|---|---|---|
| GAT | GTT | CAA | CAC | AAG | CAA | GTG | TGT | TTC | AGC | AGA | ACA | TCC | TCG | GGA | GGC | 238
| Asp | Val | Gln | His | Lys | Gln | Val | Cys | Phe | Ser | Arg | Thr | Ser | Ser | Gly | Gly |
| | 65 | | | | 70 | | | | | | 75 | | | | |
| TCA | TTT | GTG | GCT | TCT | GAT | GTC | CCA | AAT | GCT | CCC | ATA | CCT | GAT | CTC | TTC | 286
| Ser | Phe | Val | Ala | Ser | Asp | Val | Pro | Asn | Ala | Pro | Ile | Pro | Asp | Leu | Phe |
| 80 | | | | | 85 | | | | | 90 | | | | | 95 |
| CCA | CCT | GGC | CAA | ATC | ACC | GAC | CTG | AAG | GCG | GAA | ATT | CAC | GGG | GGC | AGT | 334
| Pro | Pro | Gly | Gln | Ile | Thr | Asp | Leu | Lys | Ala | Glu | Ile | His | Gly | Gly | Ser |
| | | | | 100 | | | | | 105 | | | | | 110 | |
| CTC | ATT | AAT | CTG | ACT | TGG | ACA | GCT | CCT | GGG | GAT | GAT | TAT | GAC | CAT | GGA | 382
| Leu | Ile | Asn | Leu | Thr | Trp | Thr | Ala | Pro | Gly | Asp | Asp | Tyr | Asp | His | Gly |
| | | | 115 | | | | | 120 | | | | | 125 | | |
| ACA | GCT | CAC | AAG | TAT | ATC | ATT | CGA | ATA | AGT | ACA | AGT | ATT | CTT | GAT | CTC | 430
| Thr | Ala | His | Lys | Tyr | Ile | Ile | Arg | Ile | Ser | Thr | Ser | Ile | Leu | Asp | Leu |
| | | 130 | | | | | 135 | | | | | 140 | | | |
| AGA | GAC | AAG | TTC | AAT | GAA | TCT | CTT | CAA | GTG | AAT | ACT | ACT | GCT | CTC | ATC | 478
| Arg | Asp | Lys | Phe | Asn | Glu | Ser | Leu | Gln | Val | Asn | Thr | Thr | Ala | Leu | Ile |
| | 145 | | | | | 150 | | | | | 155 | | | | |
| CCA | AAG | GAA | GCC | AAC | TCT | GAG | GAA | GTC | TTT | TTG | TTT | AAA | CCA | GAA | AAC | 526
| Pro | Lys | Glu | Ala | Asn | Ser | Glu | Glu | Val | Phe | Leu | Phe | Lys | Pro | Glu | Asn |
| 160 | | | | | 165 | | | | | 170 | | | | | 175 |
| ATT | ACT | TTT | GAA | AAT | GGC | ACA | GAT | CTT | TTC | ATT | GCT | ATT | CAG | GCT | GTT | 574
| Ile | Thr | Phe | Glu | Asn | Gly | Thr | Asp | Leu | Phe | Ile | Ala | Ile | Gln | Ala | Val |
| | | | | 180 | | | | | 185 | | | | | 190 | |
| GAT | AAG | GTC | GAT | CTG | AAA | TCA | GAA | ATA | TCC | AAC | ATT | GCA | CGA | GTA | TCT | 622
| Asp | Lys | Val | Asp | Leu | Lys | Ser | Glu | Ile | Ser | Asn | Ile | Ala | Arg | Val | Ser |
| | | | 195 | | | | | 200 | | | | | 205 | | |
| TTG | TTT | ATT | CCT | CCA | CAG | ACT | CCG | CCA | GAG | ACA | CCT | AGT | CCT | GAT | GAA | 670
| Leu | Phe | Ile | Pro | Pro | Gln | Thr | Pro | Pro | Glu | Thr | Pro | Ser | Pro | Asp | Glu |
| | | 210 | | | | | 215 | | | | | 220 | | | |
| ACG | TCT | GCT | CCT | TGT | GCCTAATATT | CATATCAACA | GCACCATTCC | TGGCATTCAC | | | | | | | 725
| Thr | Ser | Ala | Pro | Cys | | | | | | | | | | | |
| | 225 | | | | | | | | | | | | | | |

| | | | | |
|---|---|---|---|---|
| ATTTTAAAAA | TTATGTGGAA | GTGGGTAGGA | GAACTGCAGT | TGTCAATAGN CTAGGGGTGA | 785
| ATTTTGTGC | GGTGAATAAA | TAATSATTTC | ANCCTTTTTT | TGRTTATAA AAAAACGGNT | 845
| NCCCATTGGG | NNTNTNGNGG | GGGGGNNTTT | TAA | | 878

( 2 ) INFORMATION FOR SEQ ID NO:9:

( i ) SEQUENCE CHARACTERISTICS:
        ( A ) LENGTH: 228 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| | | | | | | | | | | | | | | |
|---|---|---|---|---|---|---|---|---|---|---|---|---|---|---|
| Val | Tyr | Ser | Arg | Tyr | Phe | Thr | Thr | Tyr | Asp | Thr | Asn | Gly | Arg | Tyr | Ser |
| 1 | | | | 5 | | | | | 10 | | | | | 15 |
| Val | Lys | Val | Arg | Ala | Leu | Gly | Gly | Val | Asn | Ala | Ala | Arg | Arg | Val |
| | | 20 | | | | | 25 | | | | | 30 | | |
| Ile | Pro | Gln | Gln | Ser | Gly | Ala | Leu | Tyr | Ile | Pro | Gly | Trp | Ile | Glu | Asn |
| | | | 35 | | | | | 40 | | | | | 45 | |
| Asp | Glu | Ile | Gln | Trp | Asn | Pro | Pro | Arg | Pro | Glu | Ile | Asn | Lys | Asp | Asp |
| | 50 | | | | | 55 | | | | | 60 | | | |
| Val | Gln | His | Lys | Gln | Val | Cys | Phe | Ser | Arg | Thr | Ser | Ser | Gly | Gly | Ser |
| 65 | | | | | 70 | | | | | 75 | | | | | 80 |
| Phe | Val | Ala | Ser | Asp | Val | Pro | Asn | Ala | Pro | Ile | Pro | Asp | Leu | Phe | Pro |
| | | | | 85 | | | | | 90 | | | | | 95 |

| | | | | | | | | | | | | | | |
|---|---|---|---|---|---|---|---|---|---|---|---|---|---|---|
| Pro | Gly | Gln | Ile | Thr | Asp | Leu | Lys | Ala | Glu | Ile | His | Gly | Gly | Ser | Leu |
| | | | 100 | | | | | 105 | | | | 110 | | |
| Ile | Asn | Leu | Thr | Trp | Thr | Ala | Pro | Gly | Asp | Asp | Tyr | Asp | His | Gly | Thr |
| | | 115 | | | | | 120 | | | | | 125 | | | |
| Ala | His | Lys | Tyr | Ile | Ile | Arg | Ile | Ser | Thr | Ser | Ile | Leu | Asp | Leu | Arg |
| | 130 | | | | | 135 | | | | | 140 | | | | |
| Asp | Lys | Phe | Asn | Glu | Ser | Leu | Gln | Val | Asn | Thr | Thr | Ala | Leu | Ile | Pro |
| 145 | | | | | 150 | | | | | 155 | | | | | 160 |
| Lys | Glu | Ala | Asn | Ser | Glu | Glu | Val | Phe | Leu | Phe | Lys | Pro | Glu | Asn | Ile |
| | | | | 165 | | | | | 170 | | | | | 175 | |
| Thr | Phe | Glu | Asn | Gly | Thr | Asp | Leu | Phe | Ile | Ala | Ile | Gln | Ala | Val | Asp |
| | | | 180 | | | | | 185 | | | | | 190 | | |
| Lys | Val | Asp | Leu | Lys | Ser | Glu | Ile | Ser | Asn | Ile | Ala | Arg | Val | Ser | Leu |
| | | 195 | | | | | 200 | | | | | 205 | | | |
| Phe | Ile | Pro | Pro | Gln | Thr | Pro | Pro | Glu | Thr | Pro | Ser | Pro | Asp | Glu | Thr |
| | 210 | | | | | 215 | | | | | 220 | | | | |
| Ser | Ala | Pro | Cys |
| 225 | | | |

( 2 ) INFORMATION FOR SEQ ID NO:10:

( i ) SEQUENCE CHARACTERISTICS:
        ( A ) LENGTH: 560 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..490

( i x ) FEATURE:
        ( A ) NAME/KEY: mat_peptide
        ( B ) LOCATION: 2..490

( x i ) SEQUENCE DESCRIPTION: SEQ ID NO:10:

| A | GTC | GCT | CTC | CTA | GCC | CTT | CTC | TGT | GCC | TCA | CCC | TCT | GGC | AAT | GCC | 46 |
|---|---|---|---|---|---|---|---|---|---|---|---|---|---|---|---|---|
| | Val | Ala | Leu | Leu | Ala | Leu | Leu | Cys | Ala | Ser | Pro | Ser | Gly | Asn | Ala | |
| | 1 | | | | 5 | | | | | 10 | | | | | 15 | |

| ATT | CAG | GCC | AGG | TCT | TCC | TCC | TAT | AGT | GGA | GAG | TAT | GGA | GGT | GGT | GGT | 94 |
|---|---|---|---|---|---|---|---|---|---|---|---|---|---|---|---|---|
| Ile | Gln | Ala | Arg | Ser | Ser | Ser | Tyr | Ser | Gly | Glu | Tyr | Gly | Gly | Gly | Gly | |
| | | | | 20 | | | | | 25 | | | | | 30 | | |

| GGA | AAG | CGA | TTC | TCT | CAT | TCT | GGC | AAC | CAG | TTG | GAC | GGC | CCC | ATC | ACC | 142 |
|---|---|---|---|---|---|---|---|---|---|---|---|---|---|---|---|---|
| Gly | Lys | Arg | Phe | Ser | His | Ser | Gly | Asn | Gln | Leu | Asp | Gly | Pro | Ile | Thr | |
| | | | | 35 | | | | | 40 | | | | | 45 | | |

| GCC | CTC | CGG | GTC | CGA | GTC | AAC | ACA | TAC | TAC | ATC | GTA | GGT | CTT | CAG | GTG | 190 |
|---|---|---|---|---|---|---|---|---|---|---|---|---|---|---|---|---|
| Ala | Leu | Arg | Val | Arg | Val | Asn | Thr | Tyr | Tyr | Ile | Val | Gly | Leu | Gln | Val | |
| | | 50 | | | | | 55 | | | | | 60 | | | | |

| CGC | TAT | GGC | AAG | GTG | TGG | AGC | GAC | TAT | GTG | GGT | GGT | CGC | AAC | GGA | GAC | 238 |
|---|---|---|---|---|---|---|---|---|---|---|---|---|---|---|---|---|
| Arg | Tyr | Gly | Lys | Val | Trp | Ser | Asp | Tyr | Val | Gly | Gly | Arg | Asn | Gly | Asp | |
| | 65 | | | | | 70 | | | | | 75 | | | | | |

| CTG | GAG | GAG | ATC | TTT | CTG | CAC | CCT | GGG | GAA | TCA | GTG | ATC | CAG | GTT | TCT | 286 |
|---|---|---|---|---|---|---|---|---|---|---|---|---|---|---|---|---|
| Leu | Glu | Glu | Ile | Phe | Leu | His | Pro | Gly | Glu | Ser | Val | Ile | Gln | Val | Ser | |
| 80 | | | | | 85 | | | | | 90 | | | | | 95 | |

| GGG | AAG | TAC | AAG | TGG | TAC | CTG | AAG | AAG | CTG | GTA | TTT | GTG | ACA | GAC | AAG | 334 |
|---|---|---|---|---|---|---|---|---|---|---|---|---|---|---|---|---|
| Gly | Lys | Tyr | Lys | Trp | Tyr | Leu | Lys | Lys | Leu | Val | Phe | Val | Thr | Asp | Lys | |
| | | | | 100 | | | | | 105 | | | | | 110 | | |

| GGC | CGC | TAT | CTG | TCT | TTT | GGG | AAA | GAC | AGT | GGC | ACA | AGT | TTC | AAT | GCC | 382 |
|---|---|---|---|---|---|---|---|---|---|---|---|---|---|---|---|---|
| Gly | Arg | Tyr | Leu | Ser | Phe | Gly | Lys | Asp | Ser | Gly | Thr | Ser | Phe | Asn | Ala | |
| | | | 115 | | | | | 120 | | | | | 125 | | | |

```
GTC  CCC  TTG  CAC  CCC  AAC  ACC  GTG  CTC  CGC  TTC  ATC  AGT  GGC  CGG  TCT          430
Val  Pro  Leu  His  Pro  Asn  Thr  Val  Leu  Arg  Phe  Ile  Ser  Gly  Arg  Ser
          130                      135                      140

GGT  TCT  CTC  ATC  GAT  GCC  ATT  GGC  CTG  CAC  TGG  GAT  GTT  TAC  CCC  ACT          478
Gly  Ser  Leu  Ile  Asp  Ala  Ile  Gly  Leu  His  Trp  Asp  Val  Tyr  Pro  Thr
     145                      150                      155

AGC  TGC  AGC  AGA  TGCTGAGCCT  CCTCTCCTTG  GCAGGGGCAC  TGTGATGAGG                      530
Ser  Cys  Ser  Arg
160

AGTAAGAACT  CCTTATCACT  AACCCCCATC                                                      560
```

( 2 ) INFORMATION FOR SEQ ID NO:11:

( i ) SEQUENCE CHARACTERISTICS:
        ( A ) LENGTH: 163 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Val  Ala  Leu  Leu  Ala  Leu  Leu  Cys  Ala  Ser  Pro  Ser  Gly  Asn  Ala  Ile
 1              5                        10                            15

Gln  Ala  Arg  Ser  Ser  Ser  Tyr  Ser  Gly  Glu  Tyr  Gly  Gly  Gly  Gly  Gly
               20                        25                       30

Lys  Arg  Phe  Ser  His  Ser  Gly  Asn  Gln  Leu  Asp  Gly  Pro  Ile  Thr  Ala
               35                        40                  45

Leu  Arg  Val  Arg  Val  Asn  Thr  Tyr  Tyr  Ile  Val  Gly  Leu  Gln  Val  Arg
     50                        55                       60

Tyr  Gly  Lys  Val  Trp  Ser  Asp  Tyr  Val  Gly  Gly  Arg  Asn  Gly  Asp  Leu
 65                       70                       75                       80

Glu  Glu  Ile  Phe  Leu  His  Pro  Gly  Glu  Ser  Val  Ile  Gln  Val  Ser  Gly
                    85                        90                       95

Lys  Tyr  Lys  Trp  Tyr  Leu  Lys  Lys  Leu  Val  Phe  Val  Thr  Asp  Lys  Gly
               100                      105                      110

Arg  Tyr  Leu  Ser  Phe  Gly  Lys  Asp  Ser  Gly  Thr  Ser  Phe  Asn  Ala  Val
               115                      120                      125

Pro  Leu  His  Pro  Asn  Thr  Val  Leu  Arg  Phe  Ile  Ser  Gly  Arg  Ser  Gly
     130                      135                      140

Ser  Leu  Ile  Asp  Ala  Ile  Gly  Leu  His  Trp  Asp  Val  Tyr  Pro  Thr  Ser
145                      150                      155                      160

Cys  Ser  Arg
```

( 2 ) INFORMATION FOR SEQ ID NO:12:

( i ) SEQUENCE CHARACTERISTICS:
        ( A ) LENGTH: 709 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

```
TAAACTTGCT  GTTTTGTTCC  TGTGTCTTGT  CTTTGGTTGG  TATTTCAGTA  AGTTTTTGGT      60

ATTCTCAAAT  TTTATCTAAA  TGGATAAACT  ATTAACATAG  AACATAAACC  CCAATTCTCC     120

ATTTCATTTT  TCTCTTAGGC  ATGAATCATA  CAAAACTCAA  TATAGAGCAA  TGTTTGTAAT     180

GAATTGTTCT  ATTAACAAAG  AGGAGGTTCT  AAGATATAAA  GCCTCAGAGA  ACAGGAAGAA     240

AAGGCGGGTC  CATAAGAAGA  TGAGGTCTAA  CCGGGAAGAT  GCTGCTGAGA  AGGCAGAGAC     300
```

-continued

| | | | | | |
|---|---|---|---|---|---|
| AGATGTGGAA | GAAATCTATC | ACCCAGTCAT | GTGCACTGAA | TGTTCCACTG | AAGTGGCAGT | 360 |
| TTACGACAAG | GATGAAGTCT | TTCATTTTTT | CAATGTTTTA | GCAAGCCATT | CCTAAACAGC | 420 |
| CCAACTGGCA | TTTAATTACC | CAATACTGTA | TATAAGGCAA | ATATGGACAG | TTACTTTCCT | 480 |
| CTTGCCTGTT | CATATCCTTC | AGTGACATTG | AGGAAGCAGT | GTTTCTCTTT | TTAAAGGGGA | 540 |
| ATAGTTGTCA | ACCTTCATTC | ATCTCTTACA | TCTTTCACCC | TCTCCTTTTT | TTTTTCTTTG | 600 |
| ATTTTCCCCC | TTATTGATGG | GACTGATATT | CATTCTGTTT | TTGATGAACA | TTTGGAAACT | 660 |
| GTCGGGCTTT | TTATTAAAGC | TCTGTAGAAT | TAAAATGTTC | TGGAATTAT | | 709 |

( 2 ) INFORMATION FOR SEQ ID NO:13:

( i ) SEQUENCE CHARACTERISTICS:
      ( A ) LENGTH: 570 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: CDS
      ( B ) LOCATION: 125..367

( i x ) FEATURE:
      ( A ) NAME/KEY: mat_peptide
      ( B ) LOCATION: 125..367

( x i ) SEQUENCE DESCRIPTION: SEQ ID NO:13:

```
CAGGAGGGAG AGCCTTCCCC AAGCAAACAA TCCAGAGCAG CTGTGCAAAC AACGGTGCAT      60

AAATAAGGCC TCCTGGACCA TGAATGCGAG TCCGCTGAGC TGCGTACCGG AGCCCACGGT     120

GGTC ATG GCT GCC AGA GCG CTC TGC ATG CTG GGG CTG GTC CTG GCC TTG     169
     Met Ala Ala Arg Ala Leu Cys Met Leu Gly Leu Val Leu Ala Leu
       1               5                  10                  15

CTG TCC TCC AGC TCT GCT GAG GAG TAC GTG GGC CTG TCT GCA AAC CAG     217
Leu Ser Ser Ser Ser Ala Glu Glu Tyr Val Gly Leu Ser Ala Asn Gln
             20                  25                  30

TGT GCC GTG CCA GCC AAG GAC AGG GTG GAC TGC GGC TAC CCC CAT GTC     265
Cys Ala Val Pro Ala Lys Asp Arg Val Asp Cys Gly Tyr Pro His Val
         35                  40                  45

ACC CCC AAG GAG TGC AAC AAC CGG GGC TGC TGC TTT GAC TCC AGG ATC     313
Thr Pro Lys Glu Cys Asn Asn Arg Gly Cys Cys Phe Asp Ser Arg Ile
     50                  55                  60

CCT GGA GTG CCT TGG TGT TTC AAG CCC CTG ACA GGG AAG CAG GAA TGC     361
Pro Gly Val Pro Trp Cys Phe Lys Pro Leu Thr Gly Lys Gln Glu Cys
 65                  70                  75

ACC TTC TGAGGCACCT CCAGCTGCCC CCCGGCCGGG GGATGCGAGG CTCGGAGCAC     417
Thr Phe
 80

CCTTGCCCGG CTGTGATTGC TGCCAGGCAC TGTTCATCTC AGCTTTCTG TCCCTTTGCT     477

CCCGGAAGCG CTTCTGCTGA AAGTTCATAT CTGGAGCCTG ATGTTAACG TAGTCCCATG     537

CTCCACCCGA AAAAAAAAAA AAAAAAAAA AAA                                   570
```

( 2 ) INFORMATION FOR SEQ ID NO:14:

( i ) SEQUENCE CHARACTERISTICS:
      ( A ) LENGTH: 81 amino acids
      ( B ) TYPE: amino acid
      ( D ) TOPOLOGY: linear ( i i ) MOLECULE TYPE: protein (xi) SEQUENCE DESCRIPTION: SEQ ID NO:14:

| Met | Ala | Ala | Arg | Ala | Leu | Cys | Met | Leu | Gly | Leu | Val | Leu | Ala | Leu | Leu |
|---|---|---|---|---|---|---|---|---|---|---|---|---|---|---|---|
| 1 | | | | 5 | | | | | 10 | | | | | 15 | |

| Ser | Ser | Ser | Ser | Ala | Glu | Glu | Tyr | Val | Gly | Leu | Ser | Ala | Asn | Gln | Cys |
|---|---|---|---|---|---|---|---|---|---|---|---|---|---|---|---|
| | | | 20 | | | | 25 | | | | | 30 | | | |

| Ala | Val | Pro | Ala | Lys | Asp | Arg | Val | Asp | Cys | Gly | Tyr | Pro | His | Val | Thr |
|---|---|---|---|---|---|---|---|---|---|---|---|---|---|---|---|
| | | 35 | | | | 40 | | | | | 45 | | | | |

| Pro | Lys | Glu | Cys | Asn | Asn | Arg | Gly | Cys | Cys | Phe | Asp | Ser | Arg | Ile | Pro |
|---|---|---|---|---|---|---|---|---|---|---|---|---|---|---|---|
| | 50 | | | | | 55 | | | | | 60 | | | | |

| Gly | Val | Pro | Trp | Cys | Phe | Lys | Pro | Leu | Thr | Gly | Lys | Gln | Glu | Cys | Thr |
|---|---|---|---|---|---|---|---|---|---|---|---|---|---|---|---|
| 65 | | | | | 70 | | | | | 75 | | | | | 80 |

Phe (2) INFORMATION FOR SEQ ID NO:15:

(i) SEQUENCE CHARACTERISTICS:
        (A) LENGTH: 1121 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 42..1010

(ix) FEATURE:
        (A) NAME/KEY: mat_peptide
        (B) LOCATION: 42..1010

(xi) SEQUENCE DESCRIPTION: SEQ ID NO:15:

```
AAGCTCTTCT CACAGGACCA GCCACTAGCG CAGCTCGAGC G ATG GCC TAT GTC                  53
                                             Met Ala Tyr Val
                                               1

CCC GCA CCG GGC TAC CAG CCC ACC TAC AAC CCG ACG CTG CCT TAC TAC              101
Pro Ala Pro Gly Tyr Gln Pro Thr Tyr Asn Pro Thr Leu Pro Tyr Tyr
 5               10                  15                  20

CAG CCC ATC CCG GGC GGG CTC AAC GTG GGA ATG TCT GTT TAC ATC CAA              149
Gln Pro Ile Pro Gly Gly Leu Asn Val Gly Met Ser Val Tyr Ile Gln
         25                  30                  35

GGA GTG GCC AGC GAG CAC ATG AAG CGG TTC TTC GTG AAC TTT GTG GTT              197
Gly Val Ala Ser Glu His Met Lys Arg Phe Phe Val Asn Phe Val Val
             40                  45                  50

GGG CAG GAT CCG GGC TCA GAC GTC GCC TTC CAC TTC AAT CCG CGG TTT              245
Gly Gln Asp Pro Gly Ser Asp Val Ala Phe His Phe Asn Pro Arg Phe
         55                  60                  65

GAC GGC TGG GAC AAG GTG GTC TTC AAC ACG TTG CAG GGC GGG AAG TGG              293
Asp Gly Trp Asp Lys Val Val Phe Asn Thr Leu Gln Gly Gly Lys Trp
 70                  75                  80

GGC AGC GAG GAG AGG AAG AGG AGC ATG CCC TTC AAA AAG GGT GCC GCC              341
Gly Ser Glu Glu Arg Lys Arg Ser Met Pro Phe Lys Lys Gly Ala Ala
 85                  90                  95                 100

TTT GAG CTG GTC TTC ATA GTC CTG GCT GAG CAC TAC AAG GTG GTG GTA              389
Phe Glu Leu Val Phe Ile Val Leu Ala Glu His Tyr Lys Val Val Val
                105                 110                 115

AAT GGA AAT CCC TTC TAT GAG TAC GGG CAC CGG CTT CCC CTA CAG ATG              437
Asn Gly Asn Pro Phe Tyr Glu Tyr Gly His Arg Leu Pro Leu Gln Met
             120                 125                 130

GTC ACC CAC CTG CAA GTG GAT GGG GAT CTG CAA CTT CAA TCA ATC AAC              485
Val Thr His Leu Gln Val Asp Gly Asp Leu Gln Leu Gln Ser Ile Asn
         135                 140                 145
```

```
TTC ATC GGA GGC CAG CCC CTC CGG CCC CAG GGA CCC CCG ATG ATG CCA      533
Phe Ile Gly Gly Gln Pro Leu Arg Pro Gln Gly Pro Pro Met Met Pro
    150                 155                 160

CCT TAC CCT GGT CCC GGA CAT TGC CAT CAA CAG CTG AAC AGC CTG CCC      581
Pro Tyr Pro Gly Pro Gly His Cys His Gln Gln Leu Asn Ser Leu Pro
165                     170                 175                 180

ACC ATG GAA GGA CCC CCA ACC TTC AAC CCG CCT GTG CCA TAT TTC GGG      629
Thr Met Glu Gly Pro Pro Thr Phe Asn Pro Pro Val Pro Tyr Phe Gly
                185                 190                 195

AGG CTG CAA GGA GGG CTC ACA GCT CGA AGA ACC ATC ATC ATC AAG GGC      677
Arg Leu Gln Gly Gly Leu Thr Ala Arg Arg Thr Ile Ile Ile Lys Gly
            200                 205                 210

TAT GTG CCT CCC ACA GGC AAG AGC TTT GCT ATC AAC TTC AAG GTG GGC      725
Tyr Val Pro Pro Thr Gly Lys Ser Phe Ala Ile Asn Phe Lys Val Gly
        215                 220                 225

TCC TCA GGG GAC ATA GCT CTG CAC ATT AAT CCC CGC ATG GGC AAC GGT      773
Ser Ser Gly Asp Ile Ala Leu His Ile Asn Pro Arg Met Gly Asn Gly
    230                 235                 240

ACC GTG GTC CGG AAC AGC CTT CTG AAT GGC TCG TGG GGA TCC GAG GAG      821
Thr Val Val Arg Asn Ser Leu Leu Asn Gly Ser Trp Gly Ser Glu Glu
245                 250                 255                 260

AAG AAG ATC ACC CAC AAC CCA TTT GGT CCC GGA CAG TTC TTT GAT CTG      869
Lys Lys Ile Thr His Asn Pro Phe Gly Pro Gly Gln Phe Phe Asp Leu
                265                 270                 275

TCC ATT CGC TGT GGC TTG GAT CGC TTC AAG GTT TAC GCC AAT GGC CAG      917
Ser Ile Arg Cys Gly Leu Asp Arg Phe Lys Val Tyr Ala Asn Gly Gln
            280                 285                 290

CAC CTC TTT GAC TTT GCC CAT CGC CTC TCG GCC TTC CAG AGG GTG GAC      965
His Leu Phe Asp Phe Ala His Arg Leu Ser Ala Phe Gln Arg Val Asp
        295                 300                 305

ACA TTG GAA ATC CAG GGT GAT GTC ACC TTG TCC TAT GTC CAG ATC          1010
Thr Leu Glu Ile Gln Gly Asp Val Thr Leu Ser Tyr Val Gln Ile
    310                 315                 320

TAATCTATTC CTGGGGCCAT AACTCATGGG AAAACAGAAT TATCCCCTAG GACTCCTTTC    1070

TAAGCCCCTA ATAAAATGTC TGAGGGTGTC TCAAAAAAAA AAAAAAAAA A              1121
```

(2) INFORMATION FOR SEQ ID NO:16:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO:16:

```
Met Ala Tyr Val Pro Ala Pro Gly Tyr Gln Pro Thr Tyr Asn Pro Thr
1               5                   10                  15

Leu Pro Tyr Tyr Gln Pro Ile Pro Gly Gly Leu Asn Val Gly Met Ser
            20                  25                  30

Val Tyr Ile Gln Gly Val Ala Ser Glu His Met Lys Arg Phe Phe Val
        35                  40                  45

Asn Phe Val Val Gly Gln Asp Pro Gly Ser Asp Val Ala Phe His Phe
    50                  55                  60

Asn Pro Arg Phe Asp Gly Trp Asp Lys Val Val Phe Asn Thr Leu Gln
65                  70                  75                  80

Gly Gly Lys Trp Gly Ser Glu Glu Arg Lys Arg Ser Met Pro Phe Lys
                85                  90                  95

Lys Gly Ala Ala Phe Glu Leu Val Phe Ile Val Leu Ala Glu His Tyr
            100                 105                 110
```

```
Lys Val Val Val Asn Gly Asn Pro Phe Tyr Glu Tyr Gly His Arg Leu
            115             120                 125
Pro Leu Gln Met Val Thr His Leu Gln Val Asp Gly Asp Leu Gln Leu
    130             135             140
Gln Ser Ile Asn Phe Ile Gly Gly Gln Pro Leu Arg Pro Gln Gly Pro
145                 150                 155                 160
Pro Met Met Pro Pro Tyr Pro Gly Pro Gly His Cys His Gln Gln Leu
                165                 170                 175
Asn Ser Leu Pro Thr Met Glu Gly Pro Pro Thr Phe Asn Pro Pro Val
            180                 185                 190
Pro Tyr Phe Gly Arg Leu Gln Gly Gly Leu Thr Ala Arg Arg Thr Ile
        195             200             205
Ile Ile Lys Gly Tyr Val Pro Pro Thr Gly Lys Ser Phe Ala Ile Asn
    210             215                 220
Phe Lys Val Gly Ser Ser Gly Asp Ile Ala Leu His Ile Asn Pro Arg
225             230                 235                 240
Met Gly Asn Gly Thr Val Val Arg Asn Ser Leu Leu Asn Gly Ser Trp
                245                 250                 255
Gly Ser Glu Glu Lys Lys Ile Thr His Asn Pro Phe Gly Pro Gly Gln
            260                 265                 270
Phe Phe Asp Leu Ser Ile Arg Cys Gly Leu Asp Arg Phe Lys Val Tyr
        275             280             285
Ala Asn Gly Gln His Leu Phe Asp Phe Ala His Arg Leu Ser Ala Phe
    290             295             300
Gln Arg Val Asp Thr Leu Glu Ile Gln Gly Asp Val Thr Leu Ser Tyr
305             310             315                 320
Val Gln Ile
```

( 2 ) INFORMATION FOR SEQ ID NO:17:

( i ) SEQUENCE CHARACTERISTICS:
        ( A ) LENGTH: 605 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..603

( i x ) FEATURE:
        ( A ) NAME/KEY: mat_peptide
        ( B ) LOCATION: 1..603

( x i ) SEQUENCE DESCRIPTION: SEQ ID NO:17:

```
GTT GAT ATT AAA ACC AGT GAA ACC AAA CAT GAC ACC TCT CTG AAA CCT    48
Val Asp Ile Lys Thr Ser Glu Thr Lys His Asp Thr Ser Leu Lys Pro
 1               5                  10                  15

ATT AGT GTC TCC TAC AAC CCA GCC ACA GCC AAA GAA ATT ATC AAT GTG    96
Ile Ser Val Ser Tyr Asn Pro Ala Thr Ala Lys Glu Ile Ile Asn Val
             20                  25                  30

GGG CAT TCC TTC CAT GTA AAT TTT GAG GAC AAC GAT AAC CGA TCA GTG   144
Gly His Ser Phe His Val Asn Phe Glu Asp Asn Asp Asn Arg Ser Val
         35                  40                  45

CTG AAA GGT GGT CCT TTC TCT GAC AGC TAC AGG CTC TTT CAG TTC CAT   192
Leu Lys Gly Gly Pro Phe Ser Asp Ser Tyr Arg Leu Phe Gln Phe His
     50                  55                  60

TTT CAC TGG GGC AGT ACA AAT GAG CAT GGT TCA GAA CAT ACA GTG GAT   240
```

|     |     |     |     |     |     |     |     |     |     |     |     |     |     |     |     |     |
|---|---|---|---|---|---|---|---|---|---|---|---|---|---|---|---|---|
| Phe | His | Trp | Gly | Ser | Thr | Asn | Glu | His | Gly | Ser | Glu | His | Thr | Val | Asp | |
| 65 | | | | | 70 | | | | 75 | | | | | | 80 | |
| GGA | GTC | AAA | TAT | TCT | GCC | GAG | CTT | CAC | GTG | GCT | CAC | TGG | AAT | TCT | GCA | 288 |
| Gly | Val | Lys | Tyr | Ser | Ala | Glu | Leu | His | Val | Ala | His | Trp | Asn | Ser | Ala | |
| | | | | 85 | | | | | 90 | | | | | 95 | | |
| AAG | TAC | TCC | AGC | CTT | GCT | GAA | GCT | GCC | TCA | AAG | GCT | GAT | GGT | TTG | GCA | 336 |
| Lys | Tyr | Ser | Ser | Leu | Ala | Glu | Ala | Ala | Ser | Lys | Ala | Asp | Gly | Leu | Ala | |
| | | | 100 | | | | | 105 | | | | | 110 | | | |
| GTT | ATT | GGT | GTT | TTG | ATG | AAG | GTT | GGT | GAG | GCC | AAC | CCA | AAG | CTG | CAG | 384 |
| Val | Ile | Gly | Val | Leu | Met | Lys | Val | Gly | Glu | Ala | Asn | Pro | Lys | Leu | Gln | |
| | | 115 | | | | | 120 | | | | | 125 | | | | |
| AAA | GTA | CTT | GAT | GCC | CTC | CAA | GCA | ATT | AAA | ACC | AAG | GGC | AAA | CGA | GCC | 432 |
| Lys | Val | Leu | Asp | Ala | Leu | Gln | Ala | Ile | Lys | Thr | Lys | Gly | Lys | Arg | Ala | |
| | 130 | | | | | 135 | | | | | 140 | | | | | |
| CCA | TTC | ACA | AAT | TTT | GAC | CCC | TCT | ACT | CTC | CTT | CCT | TCA | TCC | CTG | GAT | 480 |
| Pro | Phe | Thr | Asn | Phe | Asp | Pro | Ser | Thr | Leu | Leu | Pro | Ser | Ser | Leu | Asp | |
| 145 | | | | | 150 | | | | | 155 | | | | | 160 | |
| TTC | TGG | ACC | TAC | CCT | GGC | TCT | CTG | ACT | CAT | CCT | CCT | CTT | TAT | GAG | AGT | 528 |
| Phe | Trp | Thr | Tyr | Pro | Gly | Ser | Leu | Thr | His | Pro | Pro | Leu | Tyr | Glu | Ser | |
| | | | | 165 | | | | | 170 | | | | | 175 | | |
| GTA | ACT | TGG | ATC | ATC | TGT | AAG | GAG | AGC | ATC | AGT | GTC | AGT | TCA | GAG | CAG | 576 |
| Val | Thr | Trp | Ile | Ile | Cys | Lys | Glu | Ser | Ile | Ser | Val | Ser | Ser | Glu | Gln | |
| | | | 180 | | | | | 185 | | | | 190 | | | | |
| TTG | GCA | CAA | TTC | CGG | AGC | CTT | CTA | TCA | AT | | | | | | | 605 |
| Leu | Ala | Gln | Phe | Arg | Ser | Leu | Leu | Ser | | | | | | | | |
| | | 195 | | | | | 200 | | | | | | | | | |

( 2 ) INFORMATION FOR SEQ ID NO:18:

( i ) SEQUENCE CHARACTERISTICS:
        ( A ) LENGTH: 201 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

|     |     |     |     |     |     |     |     |     |     |     |     |     |     |     |
|---|---|---|---|---|---|---|---|---|---|---|---|---|---|---|
| Val | Asp | Ile | Lys | Thr | Ser | Glu | Thr | Lys | His | Asp | Thr | Ser | Leu | Lys | Pro |
| 1 | | | | 5 | | | | | 10 | | | | | 15 | |
| Ile | Ser | Val | Ser | Tyr | Asn | Pro | Ala | Thr | Ala | Lys | Glu | Ile | Ile | Asn | Val |
| | | | 20 | | | | | 25 | | | | | 30 | | |
| Gly | His | Ser | Phe | His | Val | Asn | Phe | Glu | Asp | Asn | Asp | Asn | Arg | Ser | Val |
| | | | 35 | | | | | 40 | | | | | 45 | | |
| Leu | Lys | Gly | Gly | Pro | Phe | Ser | Asp | Ser | Tyr | Arg | Leu | Phe | Gln | Phe | His |
| | 50 | | | | | 55 | | | | | 60 | | | | |
| Phe | His | Trp | Gly | Ser | Thr | Asn | Glu | His | Gly | Ser | Glu | His | Thr | Val | Asp |
| 65 | | | | | 70 | | | | 75 | | | | | | 80 |
| Gly | Val | Lys | Tyr | Ser | Ala | Glu | Leu | His | Val | Ala | His | Trp | Asn | Ser | Ala |
| | | | | 85 | | | | | 90 | | | | | 95 | |
| Lys | Tyr | Ser | Ser | Leu | Ala | Glu | Ala | Ala | Ser | Lys | Ala | Asp | Gly | Leu | Ala |
| | | | 100 | | | | | 105 | | | | | 110 | | |
| Val | Ile | Gly | Val | Leu | Met | Lys | Val | Gly | Glu | Ala | Asn | Pro | Lys | Leu | Gln |
| | | 115 | | | | | 120 | | | | | 125 | | | |
| Lys | Val | Leu | Asp | Ala | Leu | Gln | Ala | Ile | Lys | Thr | Lys | Gly | Lys | Arg | Ala |
| | 130 | | | | | 135 | | | | | 140 | | | | |
| Pro | Phe | Thr | Asn | Phe | Asp | Pro | Ser | Thr | Leu | Leu | Pro | Ser | Ser | Leu | Asp |
| 145 | | | | | 150 | | | | | 155 | | | | | 160 |
| Phe | Trp | Thr | Tyr | Pro | Gly | Ser | Leu | Thr | His | Pro | Pro | Leu | Tyr | Glu | Ser |
| | | | | 165 | | | | | 170 | | | | | 175 | |

```
Val Thr Trp Ile Ile Cys Lys Glu Ser Ile Ser Val Ser Ser Glu Gln
            180                 185                 190
Leu Ala Gln Phe Arg Ser Leu Leu Ser
        195                 200
```

( 2 ) INFORMATION FOR SEQ ID NO:19:

( i ) SEQUENCE CHARACTERISTICS:
    ( A ) LENGTH: 559 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 2..469

( i x ) FEATURE:
    ( A ) NAME/KEY: mat_peptide
    ( B ) LOCATION: 2..469

( x i ) SEQUENCE DESCRIPTION: SEQ ID NO:19:

```
C  GGC TCC GGG CGG GCG TGG CCA GTG ACT AGA AGG CGA GGC GCC GCG            46
   Gly Ser Gly Arg Ala Trp Pro Val Thr Arg Arg Arg Gly Ala Ala
   1               5                   10                  15

GGA CCA TGG CGG CGG CGG CGG ACG AGC GGA GTC CAG AGG CGA GAA GAC           94
Gly Pro Trp Arg Arg Arg Arg Thr Ser Gly Val Gln Arg Arg Glu Asp
                20                  25                  30

GAG GAA GAG GAG GAG CAG TTG GTT CTG GTG GAA TTA TCA GGA ATT ATT          142
Glu Glu Glu Glu Glu Gln Leu Val Leu Val Glu Leu Ser Gly Ile Ile
                35                  40                  45

GAT TCA GAC TTC CTC TCA AAA TGT GAA AAT AAA TGC AAG GTT TTG GGC          190
Asp Ser Asp Phe Leu Ser Lys Cys Glu Asn Lys Cys Lys Val Leu Gly
            50                  55                  60

ATT GAC ACT GAG AGG CCC ATT CTG GCA ATG GAC AGC TGT GTC TTT GCT          238
Ile Asp Thr Glu Arg Pro Ile Leu Ala Met Asp Ser Cys Val Phe Ala
65                  70                  75

GGG GAG TAT GAA GAC ACT CTA GGG ACC TGT GTT ATA TTT GAA GAA AAT          286
Gly Glu Tyr Glu Asp Thr Leu Gly Thr Cys Val Ile Phe Glu Glu Asn
80                  85                  90                  95

GTT GAA CAT GCT GAT ACA GAA GGC AAT AAT AAA ACA GTG CTA AAA TAT          334
Val Glu His Ala Asp Thr Glu Gly Asn Asn Lys Thr Val Leu Lys Tyr
                100                 105                 110

AAA TGC CAT ACA ATG AAG AAG CTC AGC ATG ACA AGA ACT CTC CTG ACA          382
Lys Cys His Thr Met Lys Lys Leu Ser Met Thr Arg Thr Leu Leu Thr
            115                 120                 125

GAG AAG AAG GAA GGA GAA GAA AAC ATA GGT GGG GTG GAA TGG CTG CAA          430
Glu Lys Lys Glu Gly Glu Glu Asn Ile Gly Gly Val Glu Trp Leu Gln
        130                 135                 140

ATA AGG ATA TGG TTT CTC CCT TTG ACC CAA CAG GTT TGT TAACTTTTCT           479
Ile Arg Ile Trp Phe Leu Pro Leu Thr Gln Gln Val Cys
    145                 150                 155

ACCATGAAAT TGAGGACGAG GAAGTGGTAG CTTTCAGCCC CGTTAAATCT TTGGATTTGG        539

GAGGGGGTGG GGTTTCAATG                                                    559
```

( 2 ) INFORMATION FOR SEQ ID NO:20:

( i ) SEQUENCE CHARACTERISTICS:
    ( A ) LENGTH: 156 amino acids
    ( B ) TYPE: amino acid
    ( D ) TOPOLOGY: linear ( i i ) MOLECULE TYPE: protein ( x i ) SEQUENCE DESCRIPTION: SEQ ID NO:20:

```
Gly Ser Gly Arg Ala Trp Pro Val Thr Arg Arg Gly Ala Ala Gly
 1               5                  10                  15

Pro Trp Arg Arg Arg Arg Thr Ser Gly Val Gln Arg Arg Glu Asp Glu
            20                  25                  30

Glu Glu Glu Glu Gln Leu Val Leu Val Glu Leu Ser Gly Ile Ile Asp
        35                  40                  45

Ser Asp Phe Leu Ser Lys Cys Glu Asn Lys Cys Lys Val Leu Gly Ile
    50                  55                  60

Asp Thr Glu Arg Pro Ile Leu Ala Met Asp Ser Cys Val Phe Ala Gly
65                  70                  75                  80

Glu Tyr Glu Asp Thr Leu Gly Thr Cys Val Ile Phe Glu Glu Asn Val
                85                  90                  95

Glu His Ala Asp Thr Glu Gly Asn Asn Lys Thr Val Leu Lys Tyr Lys
            100                 105                 110

Cys His Thr Met Lys Lys Leu Ser Met Thr Arg Thr Leu Leu Thr Glu
        115                 120                 125

Lys Lys Glu Gly Glu Glu Asn Ile Gly Gly Val Glu Trp Leu Gln Ile
    130                 135                 140

Arg Ile Trp Phe Leu Pro Leu Thr Gln Gln Val Cys
145                 150                 155
```

( 2 ) INFORMATION FOR SEQ ID NO:21:

( i ) SEQUENCE CHARACTERISTICS:
( A ) LENGTH: 409 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:21:

```
GTGGCAGAAG AAAGATAGGT TGGAGACAAT TGATTGCTCG ATGATATAAA ATGTTAAGTA    60
CCATGAATGN ATGCTGTTAG GCTGGAATGC GCCAAGATAA AAGGTGGGGC ATGGCATCAA   120
AAGGTAGGTC AACATATTAA ATAATTCCAT GTATTGAAAT ATCCAGAAAA TATATAGACA   180
GATCTATAGA GATAGAAACT GGTCTGCCCA GGACTAGGGG TTGTCTAAGG ATAAGGAGCT   240
TCTTTTTTGG ATGGTGAAAT AACCTAAAAT ATATTGTGCC ATTGTTGCA CAACTTTGTG    300
GAATATATTA AAAACCGGTT AATTGTACTC ACTAAAATGT CCTCCTTCTT AAATTTAAGC   360
TGTTNCTGG ACAAGAAAAA GGGAAAGNNA CCAAGGGGNA AAAAATTTT                409
```

( 2 ) INFORMATION FOR SEQ ID NO:22:

( i ) SEQUENCE CHARACTERISTICS:
( A ) LENGTH: 600 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:22:

```
GCCCTGGGCT TTGGGGGGGT CCCAAACATG GTATGCAGAA ATGTGATGGT TACAGGTCAG    60
TACAACCTCA GTCCTTAGAA CCCCTCCACA CTTCAGCTCT GCACCCACTT TCCTGTCATT   120
TATTTATATA GGACTGTAGT TTTTTTAGT TCGAGAGCCT TTCGAAGCTT AATTTATATT    180
CTTTCTTTGT ACCTTTTTTC TAAAATTACC AAAGATATTA CACAAAGGTA AATTAATGTT   240
```

| | | | | | |
|---|---|---|---|---|---|
| CTCTGTTTTA | TGCTTTATCT | GATGGAGGCA | AATATCCTCT | TATTGTTGAT | CAAAGGGGGC | 300
| AAAAGAATTT | AGAGGCAAAT | GAACAAGCGA | TAGGCTATTG | CAACCTGAGA | AAGAGAACTG | 360
| NTCCTTCCAT | CGTAAATTTA | GNAGNCCAAG | TAGGTAATGG | GAACCAAAGT | TGTTACTTTT | 420
| TTCTAGTAGT | TATTTTCCC | TTTTTNNTTT | TTGTGGTACC | TCTTACAGNG | NCCCAAAACT | 480
| CCATTCTCTT | TAAAGGGGTT | TTTATGGGGG | GCTTACTGCA | GGTTAAAAAT | TGGGGNCCAC | 540
| CATTTTAAA | GGGGGGCTAC | CAGAAGGGAG | GGGGGTCCCC | NTTNCNAAAA | AAAAAAATTG | 600

( 2 ) INFORMATION FOR SEQ ID NO:23:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

ATGCTTCCGG CTCGTATG                                              18

( 2 ) INFORMATION FOR SEQ ID NO:24:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

GGGTTTTCCC AGTCACGAC                                             19